United States Patent [19]
Ledez et al.

[11] Patent Number: 5,528,923
[45] Date of Patent: Jun. 25, 1996

[54] GAS AMOUNT AND SOLUBILITY INVESTIGATION APPARATUS

[76] Inventors: Kenneth M. Ledez, 33 Easterbrook Drive, Torbay, Newfoundland, Canada; Walter Snedden, 85 Barnes Road, St. Khris, Newfoundland, Canada, A1C 3X5; Henry Manson, P.O. Box 50516, R.R. #3,, St. John's, Newfoundland, Canada, A1B 4M2

[21] Appl. No.: 324,688

[22] Filed: Oct. 18, 1994

Related U.S. Application Data

[63] Continuation-in-part of Ser. No. 993,669, Dec. 21, 1992, abandoned.

[51] Int. Cl.$^6$ ............................... A61B 5/00; G01N 7/00; G01N 1/10
[52] U.S. Cl. ............... 73/19.120; 73/19.02; 73/863; 73/53.01; 73/19.05
[58] Field of Search ............... 73/19.12, 19.02, 73/19.01, 19.05, 863, 53.01

[56] References Cited

U.S. PATENT DOCUMENTS

| | | | |
|---|---|---|---|
| 2,987,912 | 6/1961 | Jacobson | 73/19 |
| 3,518,982 | 7/1970 | Timmins et al. | 128/02 |
| 3,564,901 | 2/1971 | Megrue | 73/19 |
| 3,710,778 | 1/1973 | Cornelius | 128/2 G |
| 3,922,904 | 12/1975 | Williams et al. | 73/19 |
| 3,964,864 | 6/1976 | Dahms | 23/230 |
| 4,117,727 | 10/1978 | Friswell et al. | 73/422 GC |
| 4,184,359 | 1/1980 | Gracey | 73/19 |
| 4,187,856 | 2/1980 | Hall et al. | 128/635 |
| 4,235,095 | 11/1980 | Liebermann | 73/19 |
| 4,245,494 | 1/1981 | Legendre et al. | 73/23.1 |
| 4,257,257 | 3/1981 | Dairaku et al. | 73/19 |
| 4,270,381 | 6/1981 | Demaray | 73/19 |
| 4,270,385 | 6/1981 | Demaray | 73/19 |
| 4,330,385 | 5/1982 | Arthur et al. | 204/195 R |
| 4,388,272 | 6/1983 | Gesteland | 422/102 |
| 4,468,948 | 9/1984 | Nakayama | 73/19 |
| 4,550,590 | 11/1985 | Kesson | 73/19 |
| 4,702,102 | 10/1987 | Hammerton | 73/19 |
| 4,862,729 | 9/1989 | Toda et al. | 73/19 |
| 4,944,178 | 7/1990 | Inoue et al. | 73/19.1 |
| 4,944,191 | 7/1990 | Pastrone et al. | 73/599 |
| 5,058,416 | 10/1991 | Engelhardt et al. | 73/19.01 |
| 5,062,292 | 11/1991 | Kanba et al. | 73/19.01 |
| 5,243,848 | 9/1993 | Cox et al. | 73/19.05 |
| 5,390,551 | 2/1995 | Carvajal et al. | 73/863 |
| 5,421,194 | 6/1995 | Doyle et al. | 73/53.01 |

FOREIGN PATENT DOCUMENTS

| | | |
|---|---|---|
| 1097101 | 3/1981 | Canada . |
| 1121177 | 4/1982 | Canada . |
| 1138226 | 12/1982 | Canada . |
| 4319663 | 11/1992 | Japan . |

*Primary Examiner*—Hezron E. Williams
*Assistant Examiner*—J. David Wiggins
*Attorney, Agent, or Firm*—Marcus & Associates

[57] ABSTRACT

A novel gas investigation apparatus is provided herein. Such gas investigation apparatus includes a hollow cylindrical transparent barrel having a lower inlet and an upper outlet. A plunger is slidably fitted in a leak-proof manner within the barrel. A gas inlet tube having a lower and upper inlet and outlet is provided within the plunger and extends along the longitudinal axis of the plunger. A longitudinally-extending, transparent heat transfer jacket surrounds the hollow, barrel. An upper valve is connected to the upper outlet of the barrel by means of a zero dead-space, butt-end connection. A selective entry is provided through the upper valve for admitting a study liquid or a tissue suspension into the barrel. A lower valve is connected to the lower inlet of the gas inlet tube by means of a zero dead-space, butt-end connection. An inlet conduit is provided for the selective introduction of test gas, or carrier gas, or flushing gas into the gas inlet tube through the lower valve. An inlet tube is provided for the selective introduction of a gas sample into the inlet conduit through the lower valve. An exit tube is connected to the upper valve by means of a zero dead-space, butt-end connection for leading gas exiting from the barrel to a mass spectrometer.

23 Claims, 9 Drawing Sheets

STEP 2

BLOOD SPECIMAN IS INJECTED INTO THE APPARATUS.

GAS AMOUNT AND SOLUBILITY INVESTIGATION APPARATUS

RELATED INVENTIONS

This application is a continuation-in-part of application Ser. No. 07/993,669 filed Dec. 21, 1992, the entire contents of which are incorporated herein by reference, and which application for Letters Patent became abandoned as of Nov. 15, 1994.

BACKGROUND OF THE INVENTION

1. Field of the Invention

This invention relates to an apparatus which enables the study of gas content in, and interactions with, biologic and other media, e.g., blood.

2. Description of the Prior Art

Numerous methods exist to measure gas partial pressures and gas tensions in liquids (except inert, toxic and anaesthetic gases which are more difficult), but measurement of gas content (i.e., the total amount of gas present) is more difficult. Content is a function of the partial pressure of the gas, its solubility in the material and any reactions with the material. Most methods calculate content from knowledge of the gas partial pressure, the temperature and solubility of the gas in the material being studied. In many cases however, accurate solubility data is not available and this is especially true when considering inert, toxic and anaesthetic gases. In addition, biologic and other specimens are seldom of pure, known or fixed composition. Tissue specimens are always composed of a mixture of cell types. All this could invalidate assumptions about solubility coefficients. The new apparatus enables measurement of solubilities by providing a means of saturating the material with gas and then the means to remove the contained gas permitting measurement of the amount dissolved. All this is done without the need of transfers from one container to another.

Furthermore, the design of the apparatus in the form of a modified syringe enables blood or fluid specimens to be directly aspirated from the patient with no intermediate containment vessel. This prevents any gas loss and therefore reduces errors, permitting highly accurate and reliable research to be undertaken. The apparatus is easily disassembled and sterilized for repeated use with contaminated or potentially infectious materials. The apparatus may be constructed of materials carefully chosen so as not to interact in any way with the gas or liquid under study.

An area of major importance is the determination of dissolved gases in blood, both those naturally-occurring, e.g., oxygen, carbon dioxide and nitrogen and those added for purposes of anaesthesia, e.g., isoflurane, halothane and nitrous oxide, or those used when diving under increased pressures (nitrogen, helium).

General anaesthesia has been accomplished by inhalation of the anaesthetic gas by the patient. The anaesthetic gases used are normally found, after application, as dissolved gas in the blood stream of the patient. It is extremely important that the level of the anaesthetic gas in the blood stream of a patient be rapidly and accurately determined particularly during any surgical operation.

The percentage of carbon dioxide or oxygen in the blood stream is a function of the adequacy of ventilation and the cardiovascular, respiratory and metabolic function of the patient who is under anaesthesia. It may also be a function of the level of anaesthetic gas in the blood stream, although the level of anaesthetic gas cannot be measured directly. For these and other reasons it is important to determine in vivo the level of gases dissolved in the blood stream.

Most present methods for determining the level of anaesthetic gas in the blood stream are based primarily on determining its partial pressure in gas in the lung or in the breathing system. Many physiologic dysfunctions occur which may result in these measurements not accurately representing anaesthetic gas in the blood or brain. Other gases, including carbon dioxide and oxygen are also commonly measured in respiratory gas but in this case it is possible to take samples of blood periodically and, through electrochemical laboratory analysis, determine the partial pressure or the partial pressures or percentages of the gases under consideration in the blood stream at a remote location from the patient.

The determination of naturally-occurring blood gases is also important for clinical analysis. In particular, the determination of carbon dioxide ($CO_2$) and oxygen ($O_2$) tensions in whole blood and blood serum are among the most frequently performed analysis in a clinical laboratory. Due to the great importance of these analysis, a number of techniques have been developed and are presently being used to determine $CO_2$ and $O_2$ concentration.

A knowledge of the tension of each of the gases in the human blood stream is a valuable medical diagnostic tool. A means for continually monitoring the arterial system and analyzing the blood stream gases of one or more patients, for example, in a post-operative intensive care unit, would be an extremely valuable tool for determining the condition of patients' respiratory systems and would provide an early warning of possible malfunctioning.

At the present time, the analysis of the blood stream gases is made by withdrawing an arterial or venous blood sample and, without exposing the sample to the atmosphere, expose the blood to oxygen and carbon dioxide electrodes which measure gas tension electrochemically. The mass spectrometer is not used for such routine measurements at the present time but has the advantage that virtually any gas can be easily identified and measured.

In one present method used to determine the in vivo measurement of oxygen ($pO_2$) in blood, an arterial needle which encloses an electrode assembly surrounded by a polyethylene membrane is inserted into a vein or artery. The dissolved oxygen in the blood diffuses through the membrane into an electrolytic solution and is reduced at a platinum cathode. The current produced is proportional to the oxygen content and is converted into a meter reading. However, this method has not found wide use because it is prone to many technical problems.

Numerous biomedical and other fields require knowledge of gas solubility and gas volumes in biological fluids or tissues. This is important in research in diving and aviation medicine, anaesthesia, toxicology and biochemistry. Although as mentioned above methods are available for measuring oxygen and carbon dioxide in blood and other fluids, it is more difficult to measure inert, poisonous, or anaesthetic gases or to measure gas production from various biological reactions. Existing methods for the determination of gas content in blood involve the use of the Van Slyke apparatus [using the method of D. D. Van Slyke which was published in the Journal of Biological Chemistry, Vol. 61, page 523 (1924)], vacuum extraction, gas chromatography, volumetric analysis or some combination of these preceding. In the basic Van Slyke method, blood serum and acid are mixed in a closed volume and the carbon dioxide in the blood is extracted from the blood by application of vacuum. The extracted carbon dioxide is then measured volumetrically or manometrically. When the vacuum is drawn, other blood gases are released from the serum in addition to the carbon dioxide. This requires that a base, such as sodium hydroxide, be added in order to separate the carbon dioxide from the other released gases. After this, the volumetric measurement is performed by known techniques. Few advances have been made on this methodology since 1924, with the result that gas content is seldom performed except with the above method.

Another disadvantage of most prior art techniques for measuring blood gases concerns the use of a vacuum when the reagent and blood react to release the gases to be detected. Use of a vacuum means that species other than the gas to be measured (e.g., $CO_2$) will be released. For instance, $O_2$, $N_2$, etc. will be released from the blood and will contaminate the sample measurement where it is desired to measure $CO_2$. Chemical methods are required to remove unwanted gases. However, use of these methods introduces further time-consuming procedures and other possible errors including solution or adsorption of other gases by the chemicals and unknown solubility of gases in the chemicals. It would therefore be described to provide a method which can measure numerous gases simultaneously without the need to separate one from another.

Still another disadvantage of the use of vacuum relates to the possibility of leakage and lack of vacuum tightness. In vacuum systems, errors generally occur because apparatus, e.g., valves and stopcocks, develop leaks. Since the vacuum apparatus is designed to operate reliably only when reproducibly good vacuum is provided, such techniques are critically dependent on the reliability of components which are themselves subject to numerous problems. Consequently, it is important to provide a technique which suffers only minimal interference from dissolved gases in the blood other than the species which is to be measured.

In general, such prior art methods using vacuum for measuring blood gases contain certain "non-equilibrium" features which lead to errors. The application of vacuum extracts gas from the blood which is partly reabsorbed by the blood when the vacuum is removed. Potential errors include leaks when working with high vacuums. The use of lesser vacuums can result in incomplete extraction. Leaks also occur when multiple transfers of samples between different reaction or measurement chambers are necessary. Such leaks may go undetected, especially when nitrogen or other atmospheric gases are being measured and the detection system is not gas-specific. Other problems include uncertainty that all gas has been extracted by a vacuum, inadequate control of temperature or ambient pressure and the need to make numerous assumptions or apply correction factors. In addition, many of the existing methods are highly dependent on the skill and technique of the experimenter and may suffer from inter- and intra-observer variation which is not appreciated.

In gas chromatography, the released gases are typically carried in a gas stream over a chromatographic column and then through a detector. The gas stream used as the carrier is usually He, or some other gas having a different thermal conductivity than the gases which are to be measured. The column has different affinities for each gas in the mixture and acts to separate the different gases from one another. The detector usually comprises a hot filament wire whose resistance changes in accordance with the thermal conductivity of the gas which is in contact with the wire. Since the thermal conductivities of the gases to be measured are different from the carrier gas, and since the gases have been separated in a known order, each of the transient peaks of the detector response can be associated with one of the gases to be measured. These transient responses are usually plotted on a recorder, since the measurement is a dynamic one done in accordance with the flow of gases, rather than a stationary gas measurement. The integral under the response curve or the peak height of the response curve is then a measure of the gas content in the blood sample.

While there have been numerous publications relating to gas chromatography for the determination of, for instance, $CO_2$ in blood serum, this technique has not found wide application in routine laboratory measurements. The technique is complex, requiring a significant amount of apparatus including a chromatography column, together with recording equipment. Additionally, the method is very time consuming. Part of the time consumption is due to the burdens placed on the operator of the apparatus, who has to inject the blood sample, and then wait until the sample passes through the column and the detector. The operator then has to relate the recorder output to the signal from a calibration sample, all of which is time consuming and which can lead to human error. The time involved means that results will seldom be available in time for them to be clinically useful. In this situation, gas chromatography cannot compete with electrochemical means of determining respiratory gases, or with the non-invasive methods of pulse oximetry or analysis of exhaled gases with infrared or mass spectrometry equipment.

In addition to the disadvantages noted above, gas chromatography requires the use of a separation column which is damaged by the direct injection of blood specimens. This necessitates the use of a pre-column which can be discarded as required. Also, usually high temperatures are required in the gas chromatography resulting in vaporization of the liquid and pyrolysis of biologic and other material with the possibility of producing gases in the process perhaps including the gas it is sought to study. Gas chromatography also requires a carrier gas stream. This is a dynamic measurement rather than a static measurement, and is consequently more complex and is thought to be less reliable. With such a dynamic process, constant flow rates are required and transient responses have to be quickly recorded in order to provide accurate results. While our method using mass spectrometry also employs intermittent use of a carrier gas the flow rate merely affects the rate of washout of the gases under study and does not alter the final result. In addition it would be desirable to provide a technique which measures all gases simultaneously rather than one at a time.

In addition to the above disadvantages, using gas chromatography the carrier gas has to be a gas having a different thermal conductivity than the gas species to be detected, in order that the measurement of the detected gas species is not altered by the presence of the carrier gas. It is for this reason that gases, e.g., He, which has a significantly different thermal conductivity than air, $O_2$, $N_2$, etc., are used.

Canadian Patent No. 1,097,101 patented Mar. 10, 1981 by D. P. Friswell et al. provided an automatic liquid sample-injecting apparatus for liquid chromatography. Such automatic liquid sample-injecting apparatus used a conduit, e.g. a hypodermic needle or pipette to suck liquid from a sample source and transfer it to an injector valve apparatus. The apparatus was equipped with a seal adapted to exert a radial thrust or wiping action on the conduit. Conduit working means included both a drip-proof means to supply a non-contaminating solvent for washing the exterior of the needle and means to remove such solvent, all without interfering with the use of the needle in a series of automatic injections.

Canadian Patent No. 1,121,177 patented Apr. 6, 1982 by G. Sisti et al. provided an apparatus for feeding carrier gas to gas-chromatographic columns. The apparatus included a pressure regulator to introduce gas at constant pressure and a rate regulator to introduce gas at constant flow rate, between the gas source and a fitting to the injector The regulators were positioned in parallel. A switch was provided for alternatively connecting either the pressure regulator during the injection of the sample or samples into the column, or the flow rate regulator during the subsequent processing stage inside the gas-chromatographic column.

Canadian Patent No. 1,138,226 patented Dec. 28, 1982 by J. F. Muldoon provided an improvement with respect to electronic instrumentation associated with gas chromatography systems. The patent system included a gas processor for producing a time varying signal which was related to the constituents of the gas mixture. A converter sampled the time varying signal and converted it to digital form for providing a sampled data signal. A rate of change estimator provided a rate of change signal. The estimator includes recursive digital feedback means coupled to an output of the estimator and also to the converter. In this manner, past time value signals of the estimated rate of change signal and of the sampled data signal were produced. The estimator further comprised means for combining the past time value signals with the sampled data signal for producing the estimated rate of change signal. Although this invention improved gas chromatography methods it did not improve the sample handling problems which exist when measuring gases contained in liquid.

U.S. Pat. No. 2,987,912 patented Jun. 13, 1961 by J. G. Jacobson provided a method for the determination of the amount of a gas dissolved in a liquid. The first steps in the patented method involved flushing the vessel with a neutral gas in a closed system and measuring the amount of the dissolved gas with a measuring means. The vessel was then filled to a predetermined level with the liquid to provide a constant ratio of-gas to liquid, while retaining the neutral gas in the system. The neutral gas was then circulated in the system in highly dispersed state through the liquid to extract dissolved gas from the liquid. The amount of gas dissolved in the liquid was indicated by the change in response of the measuring means after a predetermined length of time of circulation substantially shorter than needed for reaching equilibrium between the gas dissolved in the liquid and the extracted gas.

U.S. Pat. No. 3,518,982 patented Jul. 7, 1970 by R. S. Timmins et al., provided a device and method for monitoring gases in the blood stream. The patented method included the insertion of a catheter having a membrane of a material which was permeable to the gas to be measured in the blood stream. The membrane employed in the catheter had a significant rate of diffusion for at least one gaseous component of the blood stream which is to be analyzed. A gas stream of known composition and pressure, called a flush gas, was then introduced into the catheter and isolated in the chamber. Depending upon the partial pressure differences of the gaseous components on either side of the membrane wall, diffusion through the membrane occurred, which caused the normal pressure within the chamber to change with time. This pressure change was related to the concentration of the gases in the flush gas and in the blood stream to be analyzed. The pressure in the chamber at a given time was then determined, the number of pressure determinations made being at least equal to the number of gas components (n) to be analyzed in the blood stream, which components have a significant rate of diffusion through the membrane wall of the catheter. Similar pressure determinations at a given time with additional flush gases of known composition and pressure were made to obtain a series of (n+1) pressure determinations. From these pressure determinations, the value of the actual characteristic mass transport function of the gas to be analyzed could then be determined. That value was termed the "calibration factor". This calibration factor for the patient and catheter was then employed to determine the quantitative level of the dissolved gases in the blood stream continuously or intermittently.

U.S. Pat. No. 3,564,901 patented Feb. 27, 1971 by G. H. Megrue provided a system and technique for gas analysis. In the patented technique, a microgram quantity of material from predetermined meteoritic regions was volatilized in a high vacuum. The gases released from these regions were isotopically analyzed to determine their identity and abundance at each of the predetermined regions.

U.S. Pat. No. 3,710,778 patented Jan. 16, 1973 by F. L. Cornelius provided a blood gas sensor amplifier and testing system. The invention included an amplifier for processing the output signal from an in vivo sensor for the partial pressure of gas in blood. Means were provided for displaying the signal in terms of partial pressure of the gas in millimeters of mercury.

U.S. Pat. No. 3,922,904 patented Dec. 2, 1975 by D. D. Williams et al. provided a method and apparatus for detecting dissolved gases in a liquid. The method included the first step of flowing a carrier gas for displacing the dissolved gas from the liquid over a flowing body of the liquid in a confined cylindrical zone. Films of the liquid were continuously lifted into and across the flowing carrier gas to effect displacement of the dissolved gas from the liquid and to effect formation of a mixture of the carrier gas and displaced dissolved gas. The mixed gas was flowed through an operating thermal conductivity cell to relate the thermal conductivity of the mixed gas to that of the carrier gas.

U.S. Pat. No. 3,964,864 patented Jun. 22, 1976 by H. Dahms provided for a method and apparatus for the determination of $CO_2$, or $O_2$ in body fluids, e.g., blood. The technique for such determination included the first step of reacting the sample and a reagent in a vessel to release $CO_2$ into a gas space filled with air at atmospheric pressure to produce a mixture of the released $CO_2$ and air. The gas space had a volume greater than the volume of sample in the vessel. At least a portion of the mixture in the gas space was transferred to a detector by adding a displacing liquid to the vessel. The concentration of the transferred gas mixture in the detector was then measured.

U.S. Pat. No. 4,117,727 patented Oct. 3, 1978 by D. P. Friswell provided a bubble sensor for use in liquid chromatography. A sample conduit or loop which was already filled with liquid eluent communicated with the bore of a needle. The opening of the needle bore was immersed in a liquid sample so that the sample may be backfilled into the sample loop by the withdrawal of the syringe which communicated with the sample loop. After the liquid sample had been drawn into the sample conduit, the needle was lifted from the sample source and moved toward a final position in which the sample conduit was placed in parallel with a primary conduit, so that the pump which pumped the liquid eluent drove the sample from the opening toward the chromatographic column. As the needle was being raised toward this position, it was stopped at an intermediate position in which the orifice was sealed. In this condition, the liquid sample was within the sample conduit which was part of a closed space between the orifice and the syringe. The syringe was driven a small distance to reduce the volume of that space by a predetermined, programmed increment. The pressure before and after the change in the space was compared to indicate the presence or absence of a bubble in the sample.

U.S. Pat. No. 4,187,856 patented Feb. 12, 1980 by L. G. Hall et al., provided a method for analyzing various gases in the blood stream. According to the patentee, the catheter provided with a blood-blocking membrane at its distal end was equipped with a very small tube throughout its lumen which terminated in the area of the membrane. A "carrier" gas, e.g., helium, was introduced through the tube and against the interior surface of the membrane where it mixed with the blood gases passing through the membrane. The blood gases thus mixed with the carrier gas was under a small pressure and passed by viscous flow at a relatively high speed through the tubing interconnecting the catheter with the sampling input leak of the mass spectrometer. Problems with this procedure, however, may include denaturation of proteins and blood components blocking the membrane, difficulties with calibration and diffusion of carrier gas into the blood stream.

U.S. Pat. No. 4,270,381 patented Jun. 2, 1981 by D. E. Demaray provided a procedure for the measurement of gaseous products produced by microbial samples. Each sample module provided a closed reaction vessel communicating with a liquid reservoir from which displaced liquid passed to a vertical measuring column. The displaced liquid activated a float which moved a marker responsive to volume of gas produced in the reaction vessel. Plural sample modules were combined so that markers of all moved in a parallel direction upon a recording sheet moved perpendicularly thereto to provide a record of gas formation at a function of time.

U.S. Pat. No. 4,235,095 patented Nov. 25, 1980 by L. N. Liebermann provided a device for detecting gas bubbles in liquid. The detector included a pair of electromechanical transducers for disposition on a fluid-filled conduit in an acoustically-coupled relationship. An adjustable gain driving amplifier responsive to the electrical output of one transducer drove the other transducer. An automatic gain control circuit automatically adjusted the gain of the driving amplifier to maintain the system on the margin of oscillation. An indicating circuit detected modulation of the driving signal. Bubbles passing through the conduit increased the gain required to maintain the system on the margin of oscillation, and were detected as modulations of the driving signal.

U.S. Pat. No. 4,330,385 patented May 18, 1982 by R. M. Arthur et al. provided dissolved oxygen measurement instrument. The instrument included an enclosure which was partially submerged. Liquid from the main body was continuously circulated through the enclosure and an entrapped volume of air was continuously circulated through the enclosure. The amount of oxygen in this entrapped air was continuously measured by an oxygen concentration sensor which was disposed in the path of the circulating air. This provided an indirect measurement of the amount of dissolved oxygen in the liquid without actually bringing the sensor into contact with the liquid.

U.S. Pat. No. 4,468,948 patented Sep. 4, 1984 by T. Nakayama provided a method and apparatus for measuring the concentration of a gas in a liquid. The method involved passing a carrier gas through a liquid-repellent porous partition tubing, immersed in a liquid, having continuous minute channels extending through the tubing wall. The gaseous volatile substance, which passed from the liquid into the carrier gas through the continuous minute channels, was introduced into a gas detector while the flow rate and the pressure of the carrier gas were controlled by simultaneously operating both a carrier gas control means and a choking means.

U.S. Pat. No. 4,550,590 patented Nov. 5, 1988 by J. Kesson provided a method and apparatus for monitoring the concentration of gas in a liquid. The apparatus included a semi-permeable diaphragm across the face of which the liquid flowed. Gas contained in the liquid permeated through the diaphragm into a chamber and the pressure within the chamber was measured. This pressure was representative of the concentration of gas in the liquid.

U.S. Pat. No. 4,702,102 patented Oct. 27, 1987 by D. Hammerton provided an apparatus for the direct readout of gas dissolved in a liquid. The apparatus included a gas permeable tube or membrane closed at one end, and having its other end connected to a pressure sensor. The gas permeable tube was mounted on the apparatus housing such that it could be immersed in the liquid to be measured. During the measurement process, if the liquid contained less dissolved gas than -the equilibrium quantity at atmospheric pressure, it absorbed gas from within the gas permeable tube thereby changing the internal tube-gas pressure. The percentage of dissolved gas was related to the extent of gas absorption by the liquid and the resulting internal tube-gas pressure after gas absorption was substantially complete. Rapid measurement of the percentage of dissolved gas was achieved by altering the combined internal volume of the gas permeable tube and the pressure sensor to produce an optimum minimum internal volume within the combined internal volumes.

U.S. Pat. No. 4,862,729 patented Sep. 5, 1989 by K. Toda et al. provided a method for measuring the amount of gas contained in a liquid. The method included the step of introducing a liquid material into a vacuum measuring chamber. The volume of the measuring chamber was changed to provide two different liquid pressures of the liquid material in the measuring chamber. The different pressures were then detected to measure the amount of gas on the basis of Boyle's law. The apparatus included a cylindrical measuring chamber with an inlet part connecting the measuring chamber to a sample source. A valve was provided including means for closing the measuring chamber from the inlet part. A piston was fitted into the measuring chamber. A first means was provided for moving the piston a predetermined distance in the measuring chamber, the means comprising at least two cylindrical ports separated by a seal member on the piston, the cylinder ports being positioned so that the first means effected movement of the piston over the length of the measuring chamber. A pressure gauge was connected to the measuring chamber. A second means was provided for moving the piston a predetermined distance in the measuring chamber. Means were provided for detecting the location of the valve means and the piston.

U.S. Pat. No. 4,944,178 patented Jul. 31, 1990 by Y. Inoue et al. provided an apparatus and method for measuring dissolved gas in oil. In the patented method, air was blown into an oil sample through a bubble generator. Bubbles were passed through the oil sample to extract dissolved gas therefrom. A resulting air-extracted gas mixture was contacted by a gas sensor for detecting and measuring the dissolved gas. The mixture was recirculated through the oil sample.

U.S. Pat. No. 4,944,191 patented Jul. 31, 1990 by J. Pastrone et al. provided a detector to determine whether a gas is present in a liquid delivery conduit. The detector was an ultrasonic sound generator and receiver which were spaced from each other so as to receive a projecting portion of a cassette in which a liquid-carrying passage was defined by a flexible membrane. The liquid-carrying passage in the projecting portion fit between the ultrasonic sound generator and receiver, with opposite sides of the flexible membrane being in contact with the sound generator and sound receiver. The sound generator and sound receiver each included a substrate having a layer of conducting material. Two electrically isolated regions were defined on the conductive layer and a piezo-electric chip was electrically connected between the two regions. An electrical signal applied between the first and second regions excited the piezoelectric chip on the sound generator, causing it to generate an ultrasonic signal, which was transmitted through the liquid carrying passage. If liquid was present in the passage, the amplitude of the ultrasonic sound signal received by the piezoelectric chip on the sound receiver was substantially greater than when liquid was absent in the passage. The ultrasonic detector thus produced a signal indicative of liquid in the liquid carrying passage.

U.S. Pat. No. 5,062,292 patented Nov. 5, 1991 by M. Kanba et al. provided device for measuring a gas dissolved in an oil. The device included a sample container for containing a sample oil. An air bubble generator extracted the gas dissolved in the oil. A gas container contained the gas and a gas sensor detected the gas charged in the gas container. Gas measuring means was provided for measuring a concentration of the gas in response to a signal dispatched from the gas sensor. A pump supplied air to the air bubble generator.

SUMMARY OF THE INVENTION (i) Aims of the Invention

In spite of these prior patents, there is a need for a rapid and effective means to calibrate and/or monitor and/or measure the level of gases in the blood stream in tissues and in non-biologic materials. The prior art has not adequately solved the following problems, namely that certain determinations: were highly dependent on the skill of operator; used large amounts of toxic and expensive mercury, even though gas interactions with mercury may not have been known; were time consuming; and were prone to leaks and loss of sample during transfers of sample from one container to another.

An object of the present invention, then, is to provide a method and an apparatus suitable for the measurement of a specified gas carried in a liquid in a dissolved or suspended state, such method and apparatus being simple, efficient, and applicable to continuous operation and control.

Another object of this invention is to provide a method in which the determination of dissolved gas is accomplished rapidly and in a minimum of time as compared with prior procedures.

Yet another object of this invention is to provide apparatus for measuring the concentration of a gas dissolved in a liquid, the apparatus having the potential to support a high degree of automation.

Yet another object of this invention is to provide a technique for low cost, reliable measurement of $CO_2$ and $O_2$ in body fluid samples, e.g., whole blood and blood serum.

It is still another object of this invention to provide an apparatus for the measurement of $CO_2$ and $O_2$ in body fluids, which apparatus can be easily cleaned, sterilized and flushed with gas after each measurement to provide increased reliability.

It is a still further object of this invention to provide a method for measuring $CO_2$ and $O_2$ in body fluids, e.g., blood, which does not require large sample volumes.

Another object of this invention is to provide a method and apparatus for determining gas solubility and gas volumes in biological fluids or tissues which is not highly dependent on the skill and technique of the experimenter and so would not suffer from inter-observer and intra-observer variations.

Another object of this invention is to provide a method and apparatus for determining gas solubility and gas volumes in biological fluids or tissues which may be successfully and easily used to measure inert, poisonous, or anaesthetic gas or to measure gas production from various biological reactions.

(ii) Statement of Invention

By the present invention, a new apparatus and method has been provided, which has been designed to overcome many of the above problems. A computer-controlled mass spectrometer is used as the primary measuring instrument. In contrast with the prior art, very small samples can be evaluated accurately and without contamination. The apparatus may be constructed so as to permit automatic cleaning after each measurement. Further, the blood gas measured by the detector has essentially the same composition as that originally established in the vessel, thereby ensuring increased accuracy.

By this invention, a gas investigation apparatus is provided comprising: a hollow, longitudinally-extending cylindrical barrel having a lower inlet and an upper outlet, at least a portion thereof being transparent; a plunger slidably fitted in a leak-proof manner within the barrel; a gas inlet tube (e.g., about 0.01 inch bore) having a lower inlet and an upper outlet disposed within the plunger and extending along the longitudinal axis of the plunger; a longitudinally-extending, heat transfer jacket surrounding the hollow, longitudinally-extending cylindrical barrel, at least a longitudinally-extending portion thereof being transparent; an upper valve connected to the upper outlet of the barrel by means of a zero dead-space, butt-end connection; selective entry means through such valve for admitting a study liquid or tissue suspension into the barrel; a lower valve connected to the lower inlet of the gas inlet tube by means of a zero dead-space, butt-end connection; an inlet conduit for the selective introduction of test gas or carrier gas or flushing gas into such gas inlet tube through such lower valve; an inlet tube for the selective introduction of a gas sample into such gas inlet tube through such lower valve; and exit tube means connected to such upper valve by means of a zero dead-space, butt-end connection for leading gas exiting from the barrel to a mass spectrometer.

The present invention also includes the combination of the above described apparatus which is operatively connected to a mass spectrometer via the exit tube means.

(iii) Other Features of the Invention

By one feature of this invention, the cylindrical barrel and the heat transfer jacket are entirely transparent, e.g., are made of glass.

By still another feature of this invention, the plunger is formed of a rigid synthetic plastic material, e.g., an epoxy resin.

By a still further feature of this invention, the plunger is provided with a central longitudinal bore within which the gas inlet tube is situated. By a variant of such feature, the plunger is provided with a ring-shaped tip formed of a synthetic plastic material, e.g., the du Pont brand of polytetrafluoroethylene known by the trademark TEFLON. By yet another variant of such feature, the ring-shaped plunger tip is provided with a gas injection tip. By yet a still further variant of such feature, the gas inlet tube is connected at its lower end to the inlet of the bore of the plunger, and is connected at its upper end to the gas injection tip.

By another feature of this invention, the upper valve is a three-way valve or stop cock.

By yet another feature of this invention, the lower valve is a three-way valve or stop cock.

By a still further feature of this invention, the exit tube leading between the barrel and the spectrometer includes a further tube for the recycling of gas exiting the barrel back to the barrel.

By yet a further feature of this invention, a bank of interconnected valves is connected to such further tube. By a variant of such feature, one of such interconnected valves is connected to the lower valve.

By a still further feature of this invention, the lower valve includes a gas injection port.

By another specific feature of this invention, the barrel is formed of a transparent synthetic plastic material; the plunger is formed of stainless steel; the heat transfer jacket is formed of a transparent synthetic plastic material; and the inlet tube means and the exit tube means are each formed of polytetrafluoroethylene.

By still another specific feature of this invention, the syringe barrel is formed of glass; the syringe plunger is formed of an epoxy resin; the water jacket is formed of a transparent acylate resin; and the inlet tube means and the outlet tube means are each formed of polytetrafluoroethylene.

By yet another feature of this invention, the apparatus includes a temperature probe within the heat transfer jacket to measure the temperature of the heat transfer liquid.

By a still further feature of this invention, the apparatus includes a scavenger gas outlet tube connecting the upper valve of the barrel to an atmospheric pressure scavenging system by means of a zero dead-space, butt-end connection.

By still another feature of this invention, the apparatus includes a liquid trap and filter in the gas sampling exit tube leading between the barrel and the mass spectrometer.

By a further feature, the apparatus includes an ultrasonic tissue disrupter in the region of the barrel.

(iv) Advantages of the Invention

Advantages of the apparatus of this invention include the following: the provision of a special, syringe-type apparatus with the placement of a fine bore inlet incorporated into plunger, either concentrically or asymmetrically, to enable gas to be admitted to the syringe by passing above or by being bubbled through material in the syringe, depending on the orientation of the apparatus; the provision of plunger movement to enable gas or liquid to be expelled from the apparatus while still maintaining ambient pressure; the use of ambient pressure gas input to the mass spectrometer; the provision of a transparent water jacket around the apparatus to maintain temperature while being able to observe the contents of apparatus; and the allowing of equilibration of the material with gases, or the allowing of a biologic/chemical reaction to take place in the same container from which gas will be extracted by sparging with another gas.

Fundamentally the invention represents an apparatus which enables (using the methods described herein) the processing of biologic and non-biologic samples of liquids and suspensions such that the content of any gas therein may be measured without errors caused by loss of gas to or contamination by atmosphere. This makes the apparatus particularly useful in diving and hyperbaric research when atmospheric gases are being studied. The apparatus is detector-independent and/may be used with a variety of detection and measurement systems. The use of the gas amount and solubility investigation apparatus with a computer-controlled mass spectrometer will be described hereinafter. Although developed for use in medical research, the apparatus of this invention has numerous potential applications for industrial purposes where it is important to determine gas content in a liquid or suspension.

BRIEF DESCRIPTION OF THE DRAWINGS

In the accompanying drawings.

Figure 1:
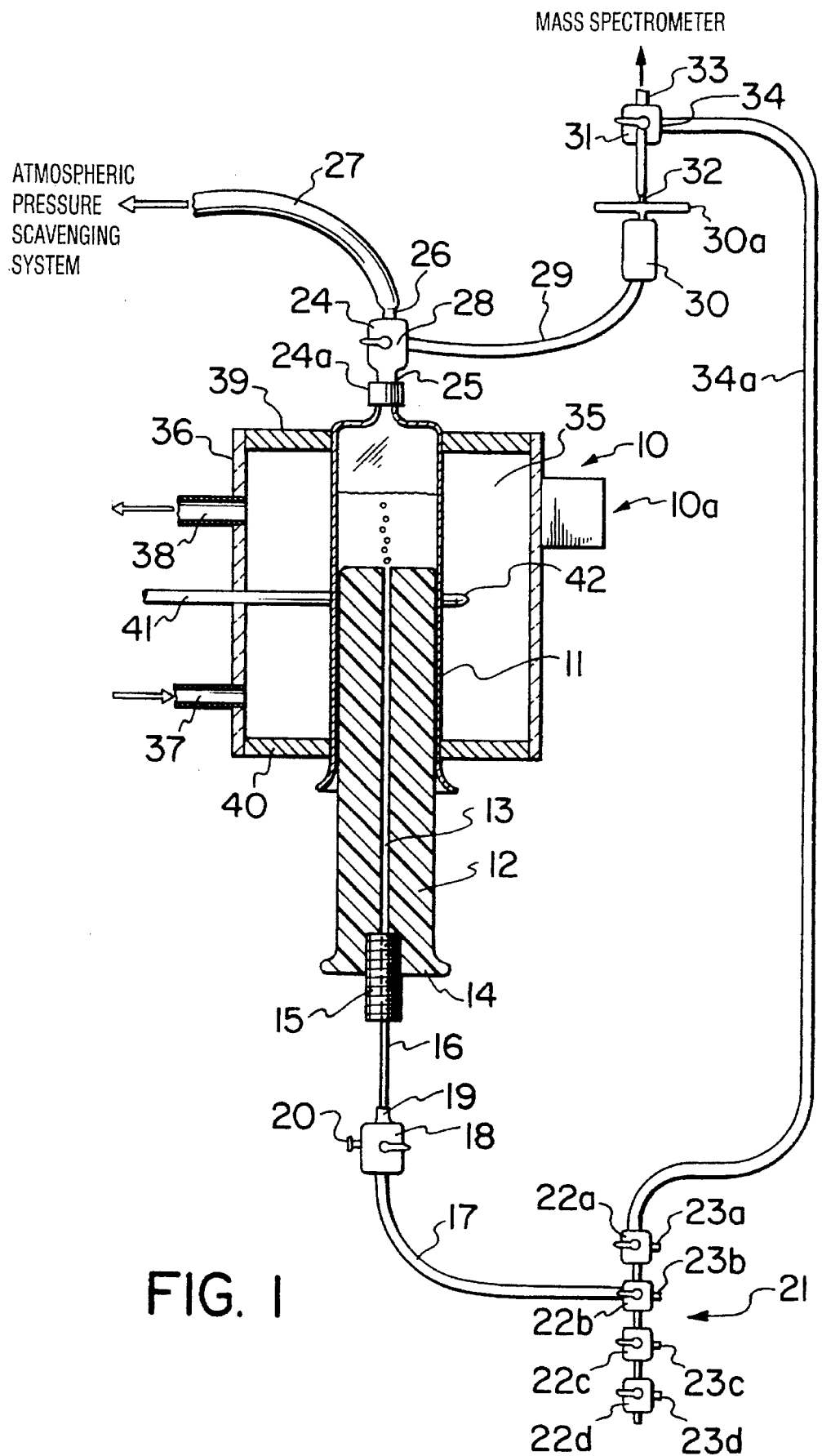
FIG. 1 is a schematic representation of the gas investigation apparatus of one embodiment of this invention.

DESCRIPTION OF PREFERRED EMBODIMENT (i) Description of FIG. 1

As seen in FIG. 1, the gas investigation apparatus 10 includes a syringe barrel 11 provided with a solid epoxy plunger 12 slidably fitted therein in a leak proof manner in a manner known to those skilled in the art. A central bore 13 is formed longitudinally through the plunger 12. Sample liquid 45, which may be admitted before assembly of the plunger within the barrel 11, or injected afterwards, is shown near the upper part of the syringe barrel 11.

At the lower exposed end 14 of the plunger 12 is a hollow bolt 15 fitted with capillary tubing 16, e.g., formed of nickel. The tubing 16 is connected to TEFLON™ tubing 17 for the introduction of a test gas or a carrier gas or a flushing gas by means of a three-way, gas-tight stopcock 18, which is connected thereto by a zero dead-space butt end junction 19. Such zero dead space butt end junction is an inert valve fitting and adaptor which is individually machined from an inert synthetic plastic material, e.g., KEL-F™, specifically designed to thread into a valve port providing a leak tight seal at 100 psi. Such valve fitting, when so threaded, does not permit any trapped volume between the valve fitting and the valve port. An injection inlet 20 for the introduction of calibration gas is provided on stopcock 18. The TEFLON™ tubing 17 is connected to a bank 21 of stopcocks 22a, 22b, 22c, 22d, each being provided with a respective gas tube 23a, 23b, 23c, 23d. By such means, selected flushing gas, or carrier gas or test gas, may be introduced into the plunger 12.

The upper end of the syringe barrel 11 includes an opening which is fitted, by means of a screw thread 24a, to a three-way gas-tight stopcock 24 using a zero dead-space butt end junction 25 (as previously described). One outlet 26 of the stopcock 24 leads via tubing 27 to an atmospheric pressure scavaging system which components are not shown in the drawings. The other outlet 28 of the stopcock 24 leads, via tubing 29 to a liquid trap 30, thence to a filter 30a and finally by a connection to three-way, gas-tight stopcock 31, via outlet 33 of stopcock 31, using a zero dead-space butt junction 32 (as previously described) to a mass spectrograph (not shown). The other outlet 34 of stopcock 31 is connected via line 34a to the bank 21 of stopcocks 23a, 23b, 23c and 23d, (previously described).

A transparent water bath 35 surrounds the syringe barrel 11. The water bath 35 includes a cylindrical wall 36 provided with water inlet line 37 and water outlet line 38. The upper and lower ends of the cylindrical wall 36 are each provided with ring-like walls 39,40, respectively, fitted thereto in a leak proof fashion in a manner well known to those skilled in the art. A temperature probe 41 and a thermometer 42 are also provided within the water bath 35.

An ultrasonic tissue disrupter 10a is provided in the region of barrel 11.

The description in FIG. 1 consequently shows entry means through an end of the barrel for admitting a study liquid or tissue suspension. The entry means are shown to be located at a barrel end along with either the inlet tube means or the exit tube.

Figure 2:
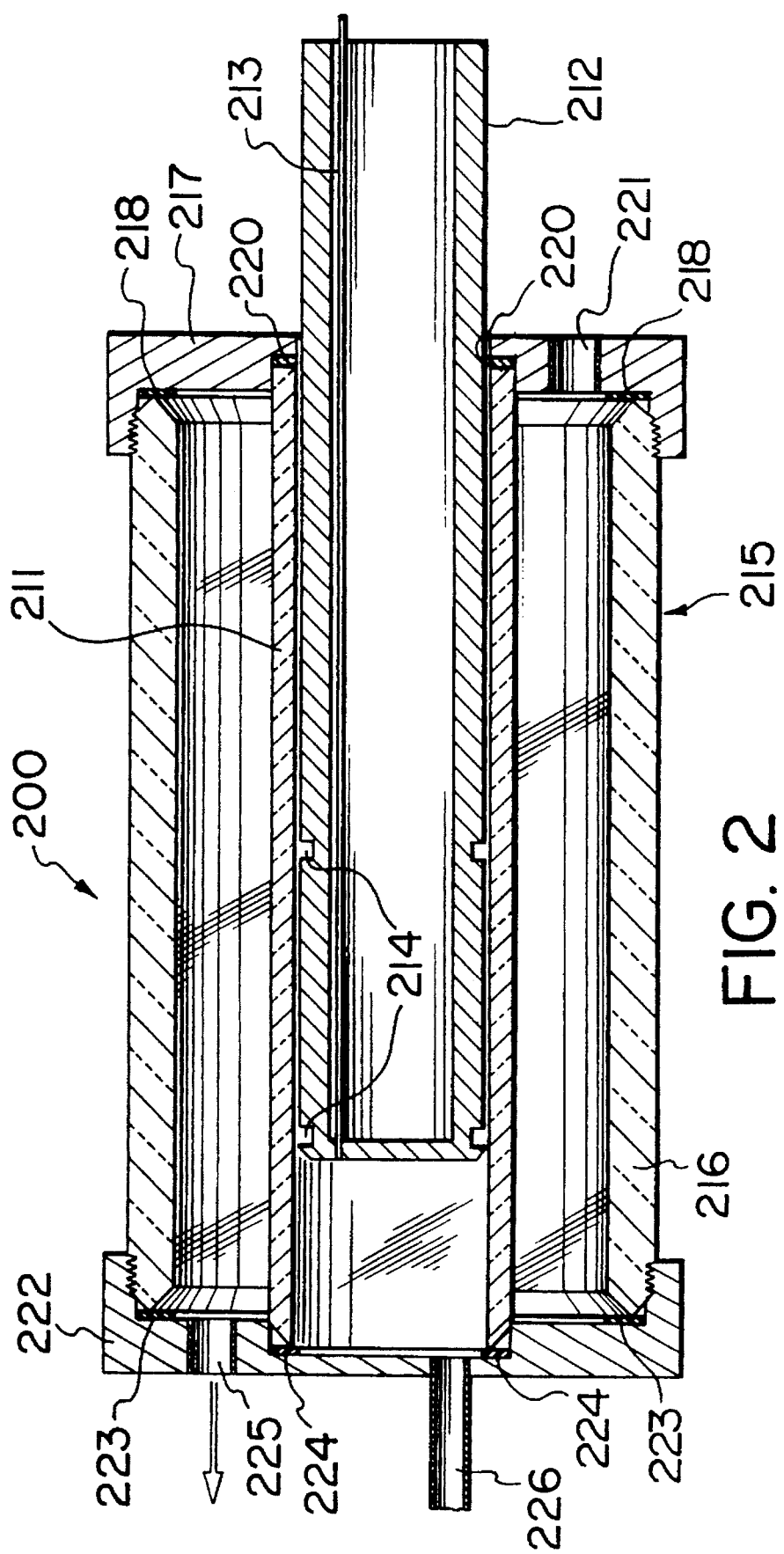
FIG. 2 is a central longitudinal sectional view of the barrel plunger portion of another embodiment of the gas investigation apparatus of this invention.

(ii) Description of FIG. 2

As seen in FIG. 2, the gas investigation apparatus 200 includes a transparent, hollow, cylindrical barrel 211, fitted with a cylindrical plunger 212, e.g., made of stainless steel. Plunger 212 is provided with an off-center capillary tube 213 for the inlet of gas. A gas-tight seal between the barrel 211 and the plunger 212 is provided by O-rings (not shown) fitted into circumferential O-ring grooves 214 in the plunger 212.

A tubular jacket 215, provided by means of a hollow transparent tube 216 is disposed concentrically around the barrel 211. An annular base 217, e.g., formed of stainless steel, is threaded to the base end of the tube 216. A first inner gasket 218 is provided between the end of the tube 216 and the inner face of base 217, and a second inner gasket 218 is provided between the end of barrel 211 and the annular base 217. A hole 220 provided in the annular base 217 allows the plunger 212 access into the barrel 211. Annular base 217 is also provided with a water inlet 221.

A cap 222, e.g., formed of stainless steel, is threaded to the head end of tube 216. A third inner gasket 223 is provided between the end of tube 216 and the inner face of cap 222, and a fourth inner gasket 224 is provided between the end of barrel 211 and the cap 222.

Cap 222 is provided with a water outlet 225, and with an off-center gas sampling tube 226.

Figure 3:
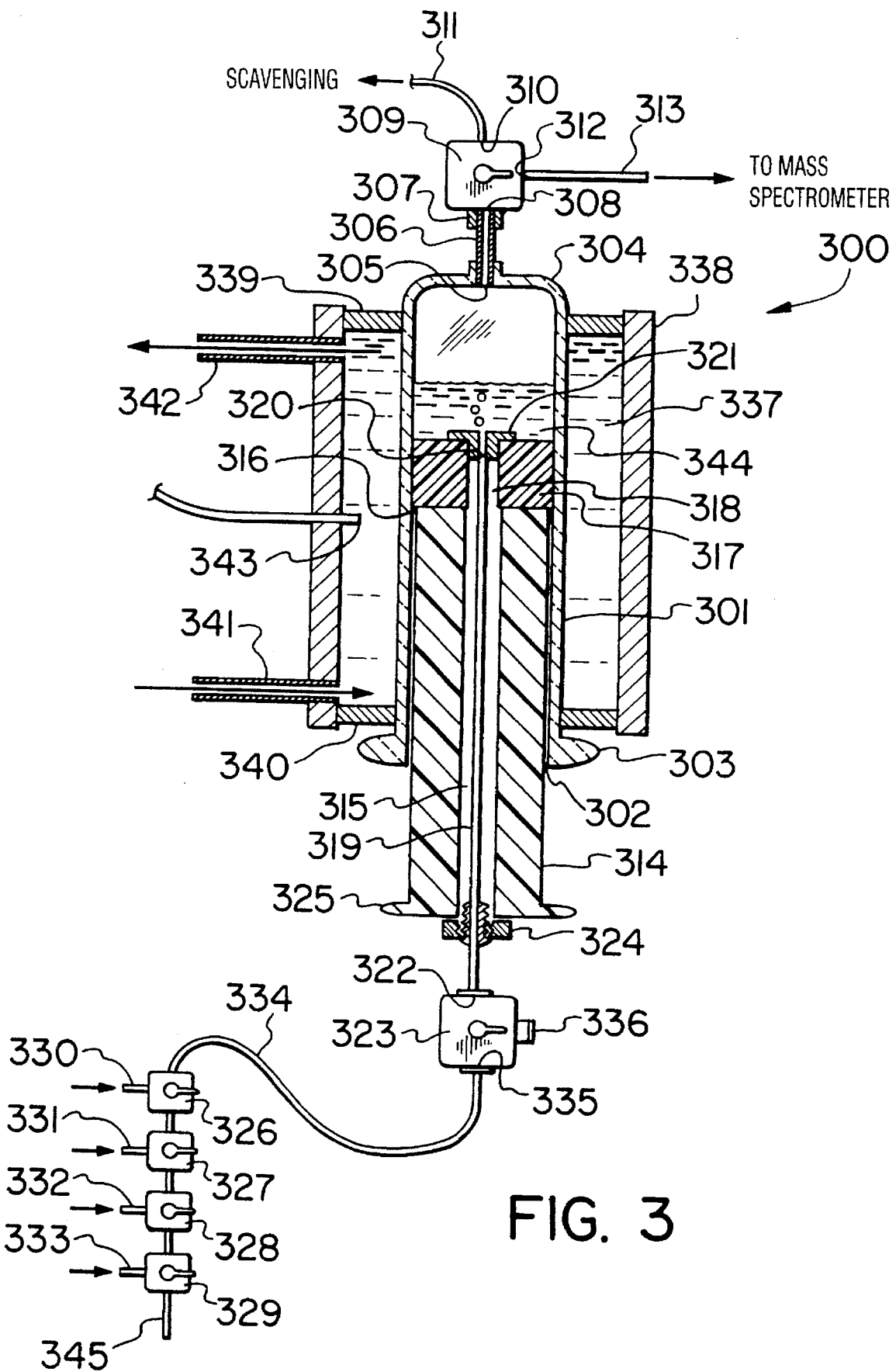
FIG. 3 is a schematic representation of the gas investigation apparatus of yet another embodiment of this invention.

(iii) Description of FIG. 3

As seen in FIG. 3, the gas investigation apparatus 300 of this embodiment of the invention includes a vertically-upright, transparent, cylindrical barrel 301 having an open lower end 302 provided with an encircling flange 303, and a closed upper end 304 which is provided with an outlet port 305 fitted with a hollow capillary tube 306.

Capillary tube 306 is provided with a valve fitting and adaptor 307 which threads into an inlet port 308 of three-way stopcock 309, providing a zero dead-space butt-end junction (as previously described) leak sealed to above 100 psi. Three way stopcock 309 is provided with a first outlet port 310 fitted, in a zero dead-space butt end junction (as previously described), to a scavanging tube 311, e.g., TEFLON™ tubing. Three way stopcock 309 is provided with a second outlet port 312 fitting, in a zero dead-space butt end junction (as previously described), to a tube 313 e.g. a TEFLON™ tube, leading a mass spectrometer (not seen).

The open lower end 302 of barrel 301 is provided with a plunger 314, e.g., formed of solid epoxy slidably fitted therein in a leak-proof manner, in a manner well known to those skilled in the art. Plunger 314 is provided with a central, vertical bore 315. The upper end 316 of plunger 314 is provided with a tip 317, e.g., made of TEFLON™, and having an aperture 318. Within the bore 315 is a gas injection capillary tube 319, e.g., formed of stainless steel, which is secured at its upper end 320 to a gas injection collar tip 321, which also is secured within the aperture 318 of the plunger tip 317. The lower end thereof is secured to an outlet port 322 of a second, lower, three-way stopcock 323 in a zero dead-space butt end junction (as previously described). Gas injection tube 319 is slidably fitted within an adaptor 324 which is threaded into the lower end 325 of the plunger 314. A bank of interconnected three-way stopcocks 326–329, is provided, with such stopcock being each fitted with a respective gas injunction tube 330–333. An outlet gas tube 334 from stopcock 326 is connected to an inlet port 335 of the second, lower stopcock 323. The lower stopcock 333 of the bank of interconnected stopcocks is provided with an inlet tube 345. All tube connections are of a zero dead-space butt end junction (as previously described). Second, lower stopcock 323 is further provided with a gas injection port 336.

The barrel 301 is surrounded by a water bath 337 defined by a cylindrical shell 338 and upper and lower seal rings 339, 340. Water bath 337 is provided with a lower inlet tube 341 and an upper outlet tube 342. Temperature within the water bath 337 is monitored by means of a thermistor 343.

As shown in FIG. 3, a study liquid 344 is disposed atop the plunger 314.

(iv) Description of FIGS. 4–7

One procedure for carrying out one testing procedure for determining the gas content of blood is described sequentially in FIGS. 4–7.

Figure 4:
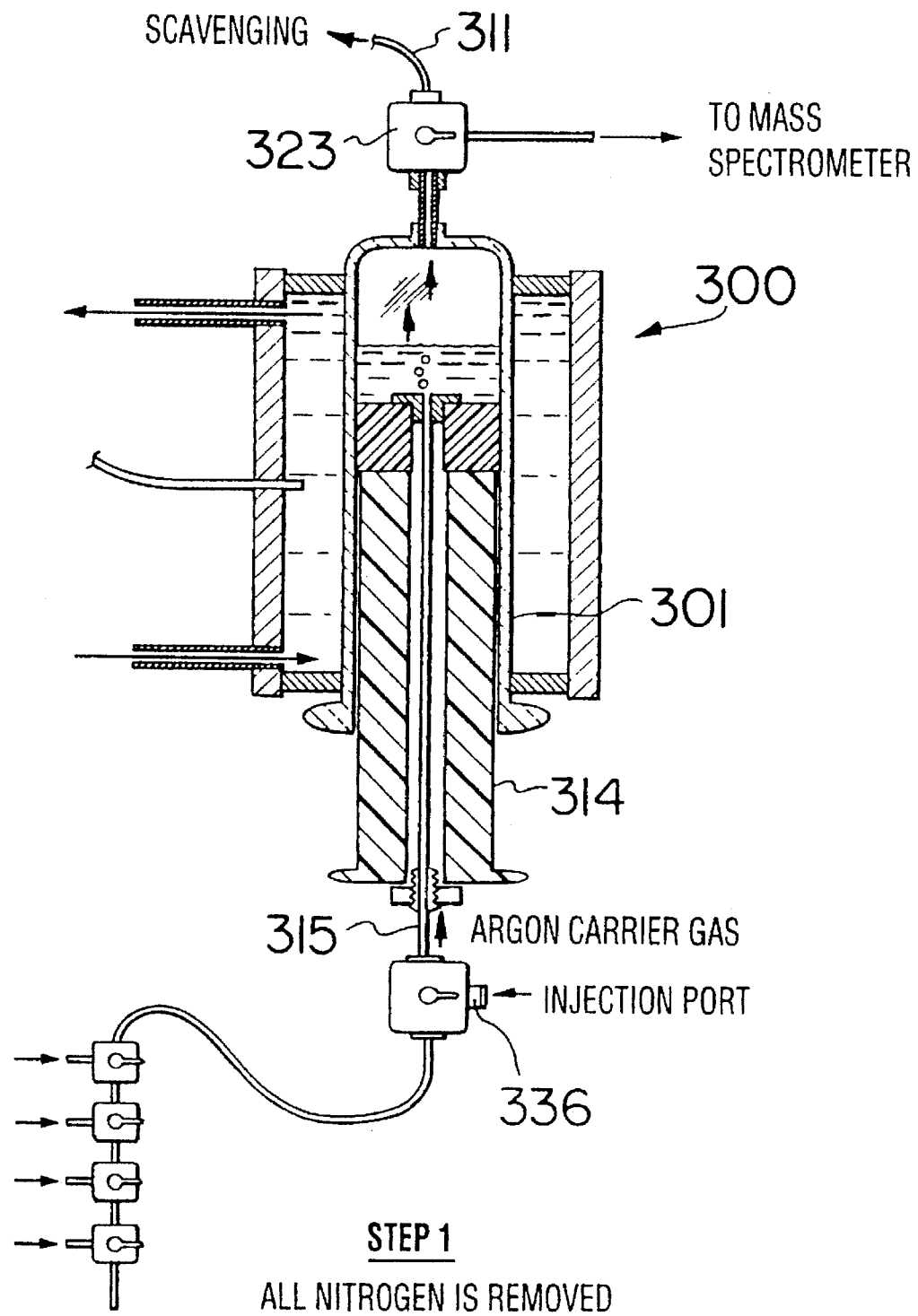
FIG. 4–7 show, schematically, some steps to be carried out in performing the method of one embodiment of this invention using the embodiment of FIG. 3 of this invention.

In FIG. 4 (Step 1) all nitrogen is removed from the apparatus by flushing with oxygen.

Figure 5:
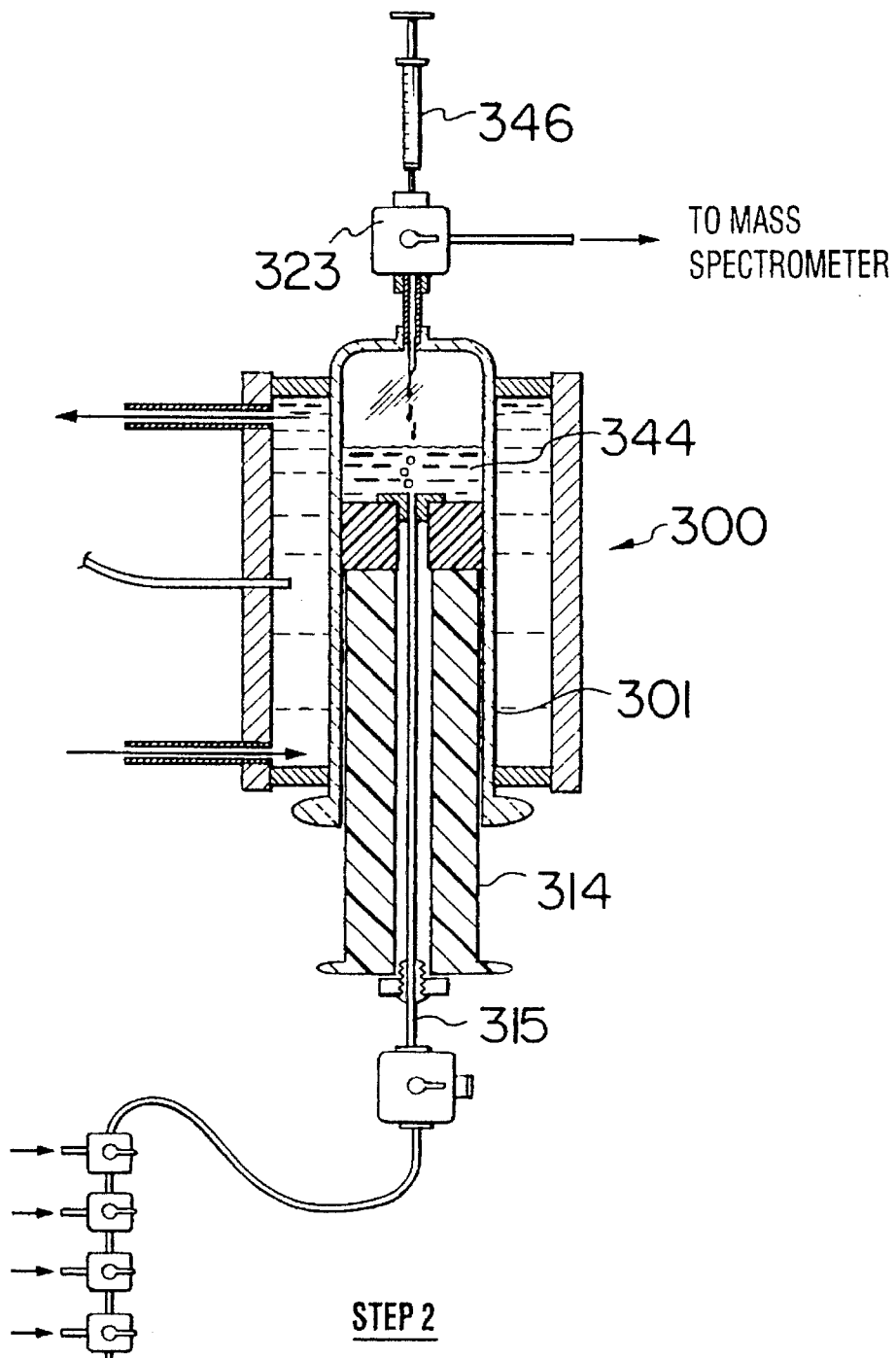

In FIG. 5 (Step 2) a blood specimen is injected into the apparatus by hypodermic 346 and through upper valve 323 to provide the study liquid.

Figure 6:
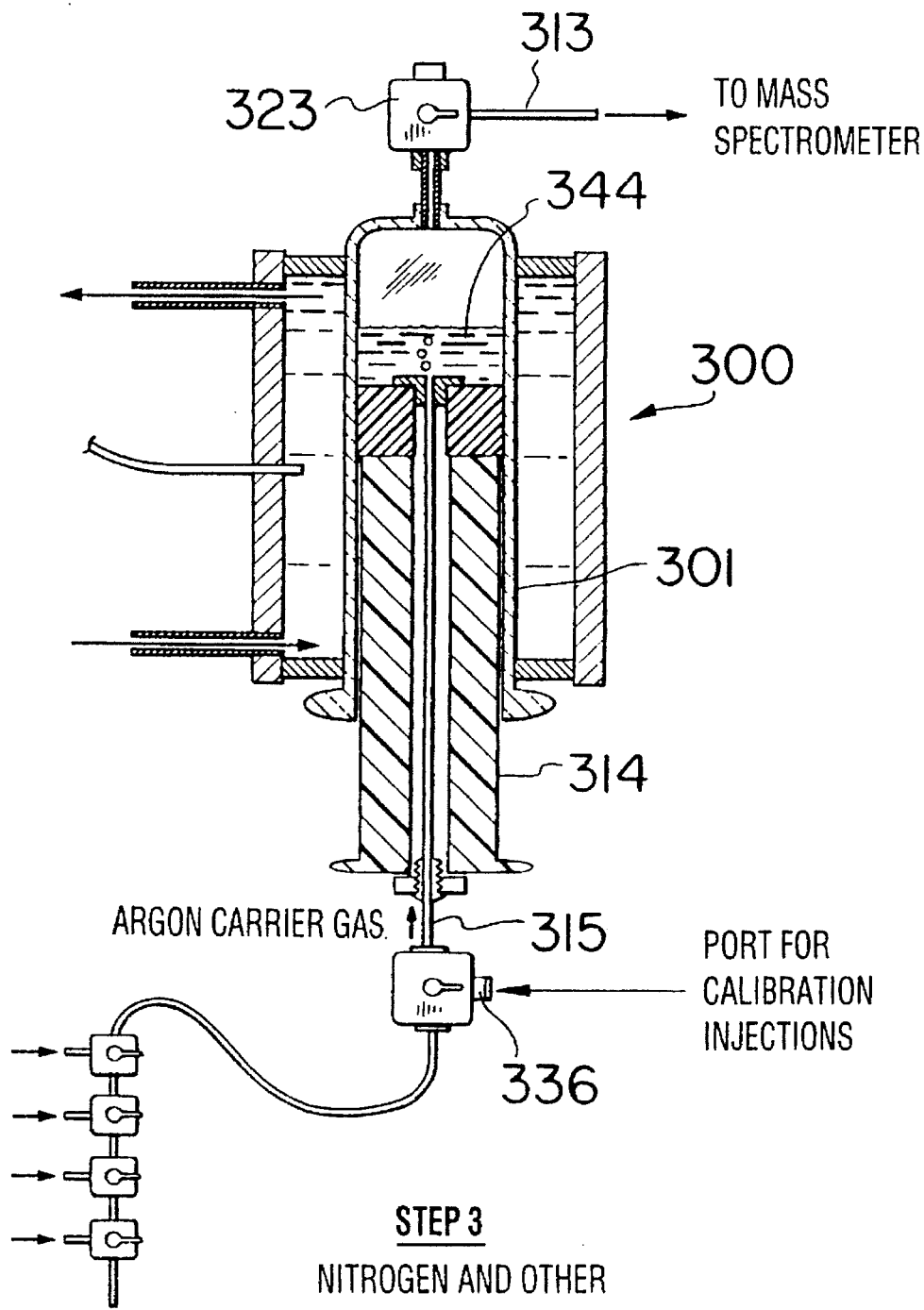

In FIG. 6 (Step 3), nitrogen and other gases are removed from the specimen (study liquid) by sparging with argon carrier gas.

Figure 7:
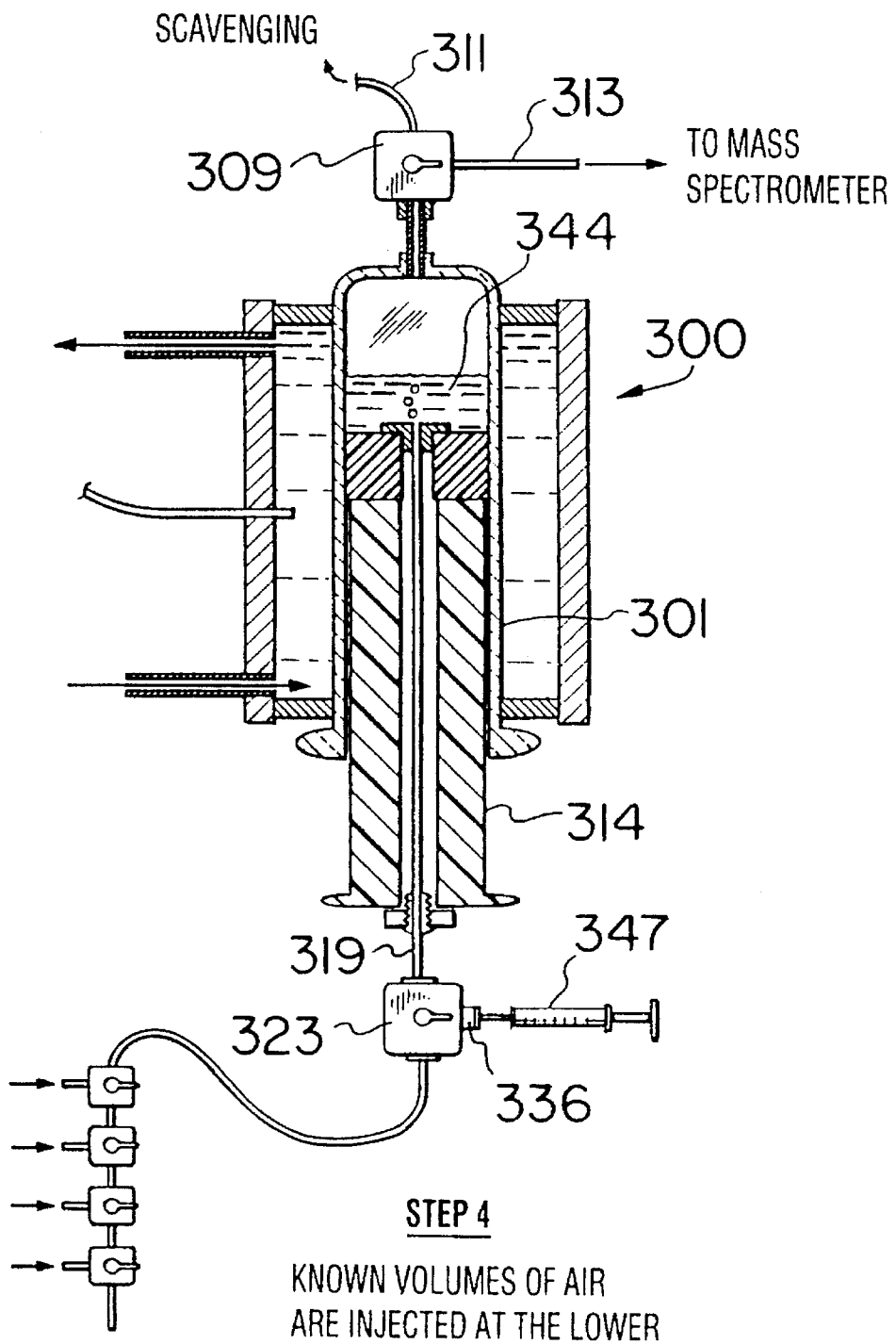

In FIG. 7 (Step 4) known volumes of oxygen are injected into the lower stopcock 323 via hypodermic 347 and sparged through the apparatus to calibrate the mass spectrometer response.

In one manner of carrying out such measurement as described above in FIGS. 4–7 may be performed as follows:

The apparatus containing 1 ml silicone antifoam solution and 5 ml headspace was purged with argon (Ar) and all gas passed through soda lime and DRIERITE™, the trademark of W. A. Hammond Drierite Co., for a special form of anhydrous calcium sulfate, (to remove $CO_2$ and water which interfere with $N_2$ measurement) and then to a computer-controlled mass spectrometer (NG Instruments, U.K.). Fresh heparinized 2 ml venous blood specimens, injected via the upper stopcock, were then sparged with Ar and extracted $N_2$ was recorded at $^m/e28$. A computer integration program was used to determine the area under the partial pressure-time curve so obtained. Calibration was performed by injection of known volumes of air via the lower stopcock and flushing this through the blood with Ar. It was found that mass spectrometer response was linear over the range of $N_2$ volumes used. Blood from 11 subjects was analyzed in triplicate with at least 4 calibration points per sample. Repeat specimens were obtained from 7 of the subjects 2–4 weeks later in order to determine within-subject variability.

Mean coefficient of variation for all 45 calibration measurements was 2.9±2.1%. Table 1 shows blood nitrogen (μl/ml) at 37° C. and 760 mmHg for replicate measurements (a;b;c;) of the first specimen for all subjects.

TABLE 1

Replicate blood nitrogen concentrations (a, b, c, μl/ml) for 11 healthy subjects breathing air at ambient pressure, together with mean, Standard Deviation (SD) and Coefficient of Variation (COV %).

| Subject | a | b | c | mean ± SD | COV |
|---------|------|------|------|------------|-----|
| 1 | 12.0 | 11.6 | — | 11.8 ± 0.2 | 1.7 |
| 2 | 12.6 | 11.7 | — | 12.2 ± 0.5 | 3.7 |
| 3 | 13.2 | 12.5 | 12.6 | 12.8 ± 0.4 | 3.0 |
| 4 | 12.8 | 12.4 | — | 12.6 ± 0.2 | 1.6 |
| 5 | 12.0 | 11.0 | — | 11.5 ± 0.5 | 4.3 |
| 6 | 10.9 | 11.0 | — | 11.0 ± 0.1 | 0.9 |
| 7 | 13.4 | 13.3 | 13.9 | 13.5 ± 0.3 | 2.4 |
| 8 | 11.3 | 11.5 | 11.2 | 11.3 ± 0.2 | 1.4 |
| 9 | 11.0 | 10.6 | 10.2 | 10.6 ± 0.4 | 3.8 |
| 10 | 11.5 | 10.8 | — | 11.2 ± 0.4 | 3.1 |
| 11 | 11.0 | 10.2 | — | 10.6 ± 0.4 | 3.8 |
| | | | mean | 11.7 ± 0.9 | |

Table 2 (below) shows the mean blood nitrogen from the first specimens of seven subjects and the mean of replicate measurements performed on blood sampled 2–4 weeks later.

TABLE 2

Comparison of mean blood nitrogen concentrations in seven healthy subjects, breathing air at ambient pressure, from specimens sampled on two separate occassions (A, B).

| | Mean $N_2$ conc. (μl/ml) | | COV between |
|---------|------------|------------|-------|
| Subject | A | B | A & B |
| 1 | 11.8 ±0 0.2 | 11.9 ± 0.4 | 0.4 |
| 2 | 12.2 ± 0.5 | 12.3 ± 0.3 | 0.4 |
| 3 | 12.8 ± 0.4 | 12.9 ± 0.6 | 0.4 |
| 4 | 12.6 ± 0.2 | 11.8 ± 0.2 | 3.3 |
| 5 | 11.5 ± 0.5 | 11.6 ± 0.4 | 0.4 |
| 6 | 11.0 ± 0.1 | 10.7 ± 0.1 | 1.4 |
| 7 | 13.5 ± 0.3 | 10.9 ± 0.3 | |

Mean within-assay coefficient of variation (n=18) was 2.7±1/0%. Mean within-subject coefficient of variation (n=6) was 1.1±1.2%, while the corresponding among-subject coefficient of variation (based on mean of A & B in Table 2) was 5.7%.

Nitrogen extraction from blood required approximately 10 minutes per specimen and results compared closely with the literature value of 11.0 μl/ml.

Figure 8:
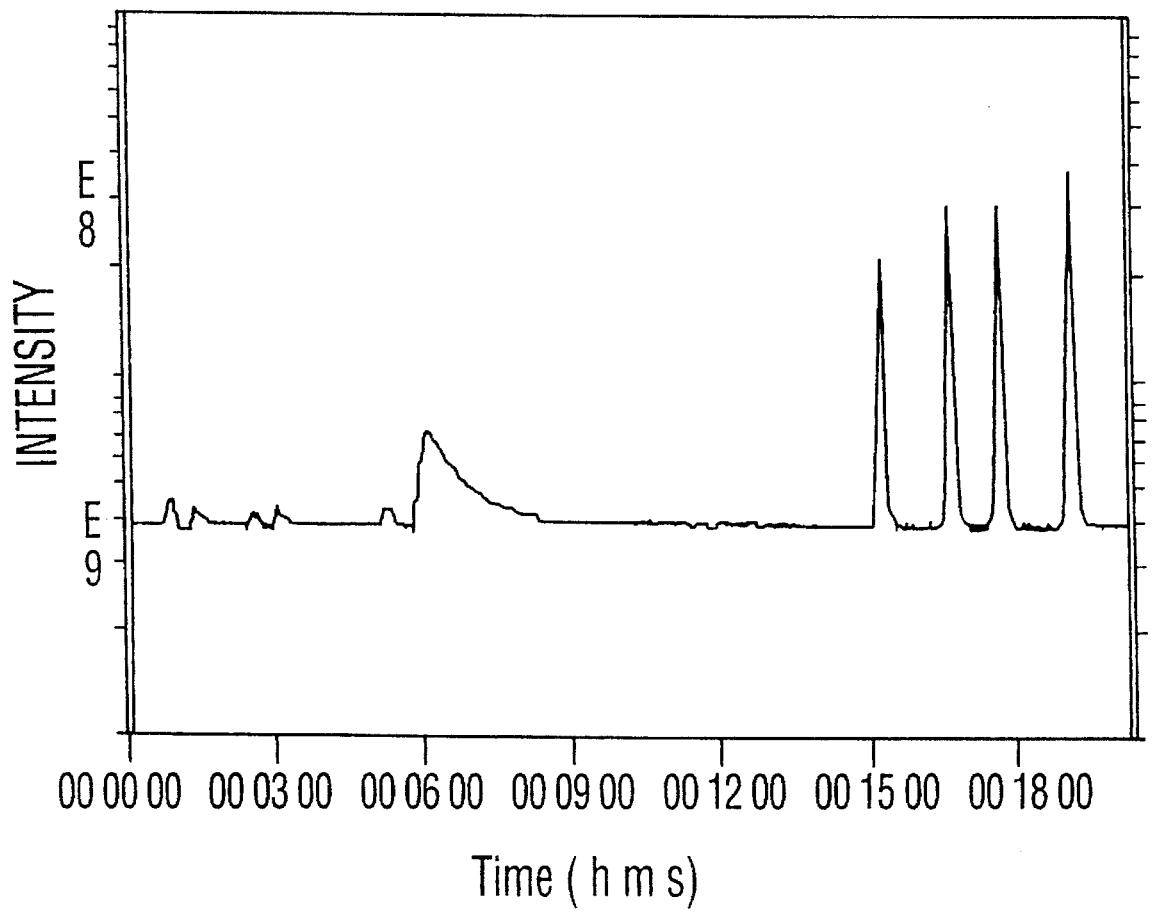
FIG. 8 is a graph illustrating the computed display for a typical blood nitrogen measurement and calibration injections.

(v) Description of FIG. 8

The graph in FIG. 8 illustrates the computer display for a typical blood nitrogen measurement and calibration injections.

Figure 9:
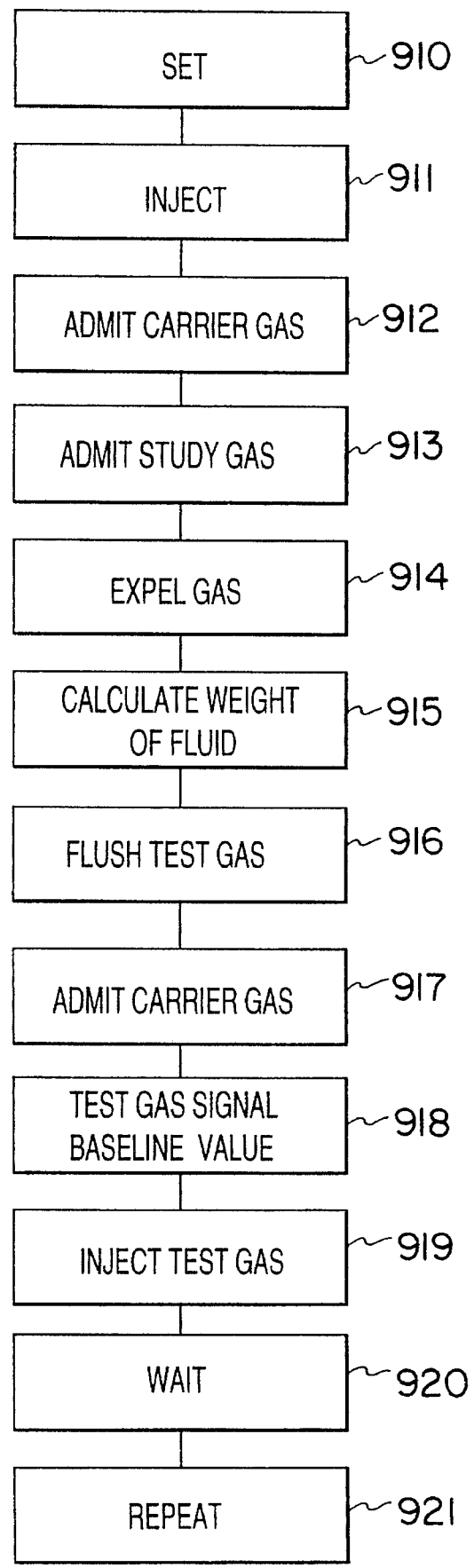
FIG. 9 is a flow chart for gas solubility measurement.

(vi) Description of FIG. 9

As seen in FIG. 9 the first step in the open solubility measurement, SET at block 910 is to set the mass spectrometer sensitivity. The next step INJECT at block 911 involves injecting a known weight of fluid at laboratory temperature into apparatus (approximately 2–4 ml volume) with headspace gas of about 20–40 ml. The next step ADMIT CARRIER GAS at block 912 involves opening the lower stopcock to admit carrier gas into the apparatus in order to sparge all other gases from the apparatus and the liquid. This is continued for about 20 minutes. The upper stopcock remains open also.

The apparatus is allowed to sit undisturbed for about 30 minutes and both stopcocks closed.

The next step ADMIT STUDY GAS at block 913 involves opening the lower stopcock and admitting the study gas and immediately opening the upper stopcock to scavenging system. The study gas may be bubbled through liquid or passed over the surface depending on the orientation of the apparatus. Gas flow rates are standardized to maintain about 100 units/min. outflow. This is continued for about 20–60 minutes.

The upper and lower stopcocks are closed and the apparatus is allowed to sit undisturbed for about 30 minutes. The fluid is observed with magnifying lens to confirm the absence of bubbles.

The next step EXPEL GAS at block 914 involves opening the upper stopcock and raising the plunger to expel all gas remaining in the syringe plus a very small quantity of liquid which is collected onto the filter. The upper stopcock is then closed.

The next step CALCULATE WEIGHT OF FLUID at block 915 involves weighing the filter to determine the weight of fluid discarded and to calculate the weight of fluid remaining.

The next step FLUSH TEST GAS at block 916 involves flushing all remaining test gas from lines. The next step ADMIT CARRIER GAS at block 917 involves opening the lower stopcock and admitting the carrier gas and allowing the plunger to descend until about 20–40 ml headspace is present. Then the plunger is fixed in place and the upper stopcock is opened towards the mass spectrometer. The flow rate of 100 units/min. on outlet is maintained.

The next step TEST GAS SIGNAL BASELINE VALUE at block 318 involves continuing to sparge all test gas from the fluid until the test gas signal on the mass spectrometer returns to its baseline value.

The next step INJECT TEST GAS at block 919 involves injecting known volumes of test gas from the gas tight syringe and injecting into the lower stopcock so that the test gas is flushed by the carrier gas through the liquid and towards the mass spectrometer.

The next step WAIT at block 920 involves waiting for the test gas signal to return to baseline.

The final step REPEAT at block 921 involves repeating the calibration procedures several times.

GENERALIZED DESCRIPTION OF THE INVENTION

The present invention provides a new, more rapid and convenient method using spectrometry for the measurement of blood nitrogen ($N_2$) or other inert gases. The apparatus consists of a modified gas-tight syringe with stopcocks at the outlet of the barrel and also on a fine bore steel tube which traverses the plunger, creating a gas inlet.

The method of the invention is highly accurate and reliable as evidenced above by the small variation in results between measurements repeated on the same subjects weeks apart.

There are many variations of the method of this invention, for example:

A) For studies during compression/decompression, the blood is sampled directly into the apparatus or to use gas-tight syringes. Gas phase separation during decompression of the sample necessitates using the entire sample to ensure it was representative of the blood of the subject. Delicate measurements requires drawing two samples simultaneously.

B) The entire apparatus may be operated inside a hyperbaric chamber while flushing all effluent gas to a mass spectrometer outside the chamber.

C) The method of this invention is useful in determining uptake and distribution of inert gases, including helium. It is known that carbon monoxide interferes with nitrogen measurement.

In general terms, moreover, one variant of the apparatus of this invention comprises a glass gas-tight syringe modified by drilling a hole in the end of the plunger and installing fine bore nickel tubing to traverse the barrel of the plunger. With this arrangement it is possible to fill the syringe with gas from either end. The syringe is surrounded by a water jacket constructed from a clear acrylate plastic (e.g., PLEXIGLASS™) cylinder. This arrangement enables the contents of the syringe and the volume scale on the barrel to be easily observed. Water is circulated between a thermostatically controlled water bath and the apparatus using a pump. Water in the water bath is continuously filtered using an aquarium filter to ensure that it remains clear and free of contaminants so that the interior of the apparatus is easily observed at all times. The interior temperature of the cylindrical water jacket is continuously monitored using a thermistor. The temperature of the interior of the syringe remains within 0.2° C. of the temperature of the surrounding water. A three-way gas-tight stopcock is attached to each end of our apparatus using zero dead-space butt-end connections. Inert TEFLON™ (the du Pont brand of polytetrafluoroethylene) tubing is used for all other connections. Several other stopcocks were attached to the lower stopcock on the apparatus without the need of making any connections or disconnections at all during measurements.

In still another embodiment of this invention, the apparatus consists of glass syringes of any size which are modified to incorporate the following features. The end of the plunger is cut off and a small hole is drilled in the flat top of the other end of the plunger which will be inside the syringe barrel and in contact with the liquid. Fine bore metal tubing is inserted into the plunger to join the hole. The barrel of the plunger is filled with liquid epoxy to hold the fine bore tubing in place. A hollow bolt is inserted into the epoxy at the end of the plunger. This enables other apparatus to be screwed onto the end of the plunger.

In yet another embodiment of this invention, the apparatus consists of special modifications to glass gas-tight syringes of any size. The modifications are similar to those described above but in this case the plunger is made of metal and the gas tight seal on the original equipment is made using gas-tight TEFLON™ seals. A hole is drilled into the TEFLON™ cap and also in the metal of the plunger base. Fine-bore tubing (about 0.01 inch bore) traverses the plunger and is silver soldered into a machined metal cap. This cap forms a seal on the TEFLON™ cap. The other end of the fine bore tube is held on the base of the plunger with a screw mechanism which tensions the fine bore tube ensuring that the metal cap in contact with the TEFLON™ is gas tight. This version of the apparatus is most satisfactory when using highly diffusible gases and non-viscous liquids or when measuring gases which have the same nominal molecular weight as atmospheric gases, leaks of which would otherwise be difficult to detect.

The barrel of the syringe is modified by incorporating a hollow bolt around zero dead-space butt-end connection and this is fixed in place with epoxy. This enables other apparatus to be screwed to the top of the syringe. With this arrangement, a bracket may be installed on the plunger and the barrel of the syringe. These brackets may be connected to each other using a variety of devices, for instance a sliding micrometer for accurate measurement of movement of the plunger or a motorized screw mechanism so that the plunger may be remotely controlled.

The whole syringe arrangement is surrounded by a clear PLEXIGLASS™ cylinder closed at each end with rubber. This cylinder has three PLEXIGLASS™ tubes of smaller diameter installed through the side. Two of these are used to circulate water to and from the inside of the cylinder to a thermostatically controlled water bath. A small water pump is used for this purpose. The third port is used for inserting a thermistor for measuring the temperature. This arrangement enables precise control of the temperature of the inside of the apparatus. The contents of the syringe and the volume gradations on the syringe barrel may be easily observed through the water jacket.

Gas-tight stopcocks are installed onto the LUER™ lock of the syringe barrel (or preferably a zero dead-space arrangement, e.g., a butt junction) and to the fine bore tubing emerging from the other end of the plunger. This arrangement enables any gas to be introduced or removed from either end of the syringe.

In one manner of use of this apparatus, the study liquid or tissue suspension is pipetted into the syringe and allowed to equilibrate to water jacket temperature for twenty minutes (equilibration usually occurs within 10 minutes). A number of factors affect the choice of volume of liquid to be used, but usually 2–4 ml is satisfactory. However, substantially smaller volumes may be used providing such volumes are measured with great precision. A carrier gas of a different nominal molecular weight to the gas under investigation is admitted into the syringe through the fine bore tubing traversing the plunger. The plunger is then withdrawn to allow adequate headspace above the surface of the liquid. The carrier gas is then bubbled through the liquid to ensure that no test gas is in solution and this may be confirmed by the absence of detectable amounts of the test gas as measured using mass spectrometry of the effluent gas. Protein containing fluids may be denatured by vigorous bubbling. This is avoided by turning the apparatus horizontally and passing the carrier gas over the surface of the liquid at a slow flow rate to avoid evaporation of water. This method requires a longer time to ensure complete removal of the trace amounts of any test gas which may already be present in the fluid. The test gas is then admitted to the syringe apparatus from below. Two basic methods have been used for saturizing the liquid with gas, namely bubbling and incubation. A third method was to combine these two.

In the bubbling mode, the test gas is bubbled through the liquid under study and this results in saturation within twenty minutes in all cases, and usually within five or ten minutes. The duration of time required varies according to a number of factors, namely: rate of gas flow/bubbling; solubility of the gas in the liquid; diffusibility of the gas; volume of liquid; volume of syringe used; and size of bubbles employed.

In addition to bubbling, the whole apparatus may be shaken by a mechanical shaker to improve mixing. Although many factors may determine the time needed to attain saturation it is easy to determine for each combination of circumstances how long is required by finding the time after which no further accumulation of gas in solution occurs as determined during the measurement stage. However, it has been found that fifteen minutes of bubbling is more than enough for even the most insoluble gas. The potential concerns with this method are that any bubbles of test gas which are not dissolved will be measured during the extraction stage and thus give a falsely high reading. In addition, it is known that the pressure inside bubbles, especially small bubbles is higher than the gas tension and hydrostatic pressure in the liquid and this leads to the possibility of supersaturation occurring inadvertently. However, by using the atmospheric pressure incubation mode described below it has been shown that the bubbling mode as described does not result in supersaturation with any gas.

In the incubation mode, the whole apparatus can be rotated so that it is horizontal, while still being clamped to a electric shaking machine. When incubation is being used for equilibration, a 50 ml syringe apparatus is employed in which the fine bore tubing is installed asymmetrically near one side of the plunger. In this way, when the apparatus is horizontal on one side test gas can flow over the top of the liquid without bubbling through it. Shaking the apparatus then causes waves on the surface of the liquid but no bubbling. Incubation requires a longer period of time for full saturation of the test liquid but obviates concerns of supersaturation so long as atmospheric pressure is maintained within the syringe. By this means it was shown that supersaturation does not occur with bubbling methods described above because no further solution of gases occurred as compared with ambient pressure incubation modes.

All effluent gases are scavenged to a passive atmospheric system and it was shown that pressure inside the syringe never exceeded 2 mm water above atmospheric.

In the use of the present apparatus, gas in solution is removed by sparging the fluid with a carrier gas of different nominal molecular weight to the gas under study. This method has been employed for many years for de-gassing fluids but has not been little used for extracting gas for measurement. There are several mechanisms whereby this process works. Firstly, bubbles of carrier gas contain none of the study gas and therefore the latter will diffuse into the bubbles. Bubbles are buoyant and rise to the surface and burst thereby releasing study gas into the headspace above the surface of the liquid. There may also be a streaming effect whereby the study gas is carried along in the stream of gas flow, especially when using non-volatile solvents. In addition it is possible that vigorous bubbling imparts additional kinetic energy to the gas molecules enhancing diffusion. The constant stream of carrier gas also flushes the headspace of any test gas to that a diffusion gradient exists between the gas phase and the liquid phase near the surface. As gas diffuses from the surface this creates a concentration gradient within the liquid which will result in diffusion of gas in solution towards the surface. The constant stream of bubbles also has a stirring effect.

In yet a further method of use of this apparatus, the apparatus may be used for measuring the solubility of a gas in a liquid.

The liquid is placed inside the disassembled syringe, and the syringe plunger is then inserted to assemble the syringe. The apparatus is then placed in an inverted vertical position, and is held in that position by a clamp on the water jacket, and if desired this can be attached to a laboratory stand or electric shaking equipment. A separate clamp holds the plunger in the desired position.

The test gas is introduced via the stopcock and fine bore tubing and bubbles through the liquid from the bottom. A gas head space exists above the surface of the liquid and excess gas exits through the top and the stopcock and out to an atmospheric scavenging system. When full equilibration has occurred both stopcocks are closed and the apparatus is allowed to sit undisturbed to ensure that all bubbles in the fluid have dissipated. After this the plunger of the syringe is elevated and the head space gas and a very small quantity of the test liquid is expelled through the stopcock towards the scavenging system. Then a carrier gas which is different than the test gas is introduced through the fine bore tubing to once again create a head space of gas above the surface of the liquid. The position of the stopcock is changed so that all gas flowing out of the top of the syringe and the stopcock is directed towards the measuring apparatus rather than the scavenging system. The carrier gas is then bubbled through the test liquid from below and this sparges all of the test gas out of the liquid so that the amount may be measured, for instance using a mass spectrometer or gas chromatography.

By incorporating an ultrasonic nebulizer into the apparatus of this invention it is possible, in addition, to disrupt cells and tissues in a controlled gas environment or to study gas uptake into or production by tissues. Studies with blood are easily undertaken by the addition of anti-foaming agents. The apparatus may also be used to measure gases in non-biological fluids such as petrochemicals.

As described above, the present invention has provided a novel apparatus which enables all reactions, equilibrations, extractions and calibrations to be made using the same container. This reduces the risks of leaks and losing the gases under investigation during transfers. Among the advantages of this apparatus are the following: the apparatus has low/zero deadspace enabling high precision measurements for scientific research; biological or chemical reactions, gas equilibration and gas extraction all take place using the same container, so that the transfers between vessels are required, thereby reducing the risks of leaks or loss of sample; the contents of the apparatus may be easily viewed at all times; only a small sample of liquid or tissue is required, usually 5 ml or less; ambient pressure is maintained at all times, thereby avoiding leaks of atmospheric gases into the apparatus and leaks out of the apparatus; excellent temperature control and stability is maintained; the asymmetric placement of fine-bore tubing through the plunger of the syringe enables gas to either bubble through the liquid or to flow over the surface simply by tilting the apparatus so that a combination of the bubbling and incubation methods of gas equilibration may also be used; using the multiple ion monitoring mode on the mass spectrometer with the apparatus enables leaks of atmospheric gases into the apparatus to be detected; the apparatus may be used for liquids, colloids, blood, or tissue suspensions; an ultrasonic tissue disrupter may be incorporated into the plunger of the syringe apparatus enabling homogenates to be prepared without exposure to the atmosphere; the apparatus may be used for volatile liquids by using cold water to cool the apparatus; the apparatus may be used for determining solubility or gas content in a liquid; the apparatus may be used for highly toxic gases as leaks are readily detected and effluent gas is readily scavenged; and because ambient pressure is maintained at all times, the risks of leaks out of the apparatus is minimized; direct contact of carrier gas with the liquid under study permits very efficient extraction of gas; the plunger may be moved to expel one gas or liquid from the apparatus and admit another, which enables more rapid equilibration of gas with liquid, and since the liquid never comes into contact with gas or atmosphere other than that selected, once equilibration has occurred there is no risk of losing gas from solution to another gas space prior to measurement of gas content; no liquid comes into contact with the study gas or study liquid and therefore there is no risk of losing gas into solution into another liquid; the whole process may be automated; the apparatus may be conveniently used for measuring solubility of content of inert, toxic, anaesthetic or other gases in fluids and tissue suspensions; atmospheric pressure may be maintained without interfering with the reaction inside the apparatus; hermetic sealing is easily accomplished enabling even highly toxic gases to be studied; no vacuum extraction is required and the test liquids and gases need not be transferred from one container to another with all the inherent risks of leaks and loss of test material; for many gas-liquid combinations, the apparatus and methodology enables much faster measurements than those in current use; the temperature may be carefully controlled; the contents of the apparatus may be easily observed during any experiment; different carrier and test gases may be introduced into either end of the apparatus without the need for making any connections or disconnections, which is important for instance when working with toxic gases or with gases which are abundant in the atmosphere, since any leaks in these situations would be either dangerous or introduce significant errors into the experiment; biological reactions which produce gas may be studied, for instance by having tissue or enzyme suspensions in the syringe; measurement of virtually any gas may be used when used with a mass spectrometer, including the amount of gas that is contained in another material; it provides means to saturate a material with any gas, including atmospheric and toxic gases and determine solubility; it provides convenient, leak-free handling of gas; it may be used with toxic gases; it does not employ toxic mercury; it could be used in industries, e.g., petro chemicals, where gases must be measured in liquids; it could be used clinically to measure toxic gases in blood; the apparatus is most suitable for use with continuous flow gas analyzers such as a mass spectrometer and requires modification for use with intermittent apparatus such as gas chromatographs; the plunger may be machined from stainless steel (or other materials) and fitted with double inert O-rings, or double TEFLON™ seals as commonly used in gas-tight syringes, to create gas-tight seal; the barrel of the apparatus and the water jacket may be made from glass, polycarbonate or other materials; the top of the barrel may have various parts machined from stainless steel and fitted to apparatus using O-ring seal.

When the nominal molecular weight of a gas under research is the same as another gas present in the system it is possible usually for research purposes and using the gas investigation apparatus here described to use a non-radioactive isotope of the gas to permit easier separation and measurement.

The apparatus and method of the present invention may be used in laboratories in the fields of medicine toxicology, biology and chemistry, whenever it is necessary to measure the solubility or content of any gas in a liquid or tissue suspension, e.g., blood. Current methods require multiple transfers of the test liquid and/or vacuum extraction of the gas. Leaks may occur at each step and it is difficult to measure the pressure inside the reaction or test vessels and thereby calculate solubility coefficients or convert to standard temperature and pressure (STP). With our apparatus the reaction or gas equilibration may take place in the same container that the gas will be extracted from while maintaining atmospheric pressure. This enables greater accuracy and sensitivity when measuring the gas using, for instance, a mass spectrometer or gas chromatography.

The apparatus is a specially constructed syringe with water jacket, zero dead-space stopcocks and fittings, with gas inlets and other apparatus incorporated into the moveable plunger. It is used to saturate liquids, cell suspensions or other materials with gases and/or extract gases from the aforementioned to enable their measurement. All this is done without contaminating the interior of the apparatus with atmosphere or vice-versa.

Leaks may exist from the syringe apparatus or its connections. To check for this possibility the following methods were used.

The whole apparatus is tested for leaks from the apparatus in the following manner. The whole apparatus is submerged so that it was covered by one centimeter of water. The apparatus is then pressurized to 300 mmHg above ambient. Ambient pressure was measured with a mercury barometer. The reservoir of the barometer was connected to one of the stopcocks of our apparatus using. TEFLON™ tubing and the pressure inside was increased by admitting various gases (including helium) into the equipment until the pressure approximated 300 mmHg above ambient. All parts of the apparatus were carefully inspected for bubbles. A similar procedure was performed with the apparatus in air by brushing soap solution over all connections and the syringe barrel and observing for bubbles. Lastly, when pressurized with helium the air around the apparatus was sampled by the mass spectrometer.

In order to test for leaks into the apparatus in the following manner, the mass spectrometer was used in multiple ion monitoring mode and at least one atmospheric gas was monitored during every measurement. If nitrogen was being studied then oxygen was also monitored and vice-versa. If other gases were being studied then oxygen and/or nitrogen was also monitored. Thus, leaks of atmospheric gases into the apparatus were readily apparent simply by measuring an atmospheric gas of different nominal molecular weight to the gas being studied. In addition, while conducting calibrations and experiments a flow of either carbon dioxide or helium was directed towards the base of the syringe apparatus (considered the most likely place for a leak to occur) and the presence of this gas in the syringe effluent was determined by the mass spectrometer. This procedure was repeated after reducing the pressure inside the apparatus to 300 mmHg below ambient. Finally, with the apparatus still at 300 mmHg below ambient pressure the entire assembly was submerged below water to a depth of ten centimeters and held down for ten minutes. After being removed from the water the interior of the apparatus was flushed with dry argon gas and the effluent monitored for the presence of water vapour.

Calibration for gas volume is performed under conditions which closely resembled those of each experiment. Between six and nine calibrations were performed immediately following each experimental run using known volumes of the test gas injected from a gas tight syringe using volumes which spanned the anticipated volume of test gas dissolved in the liquid. This was done using two different methods. In each, the calibration volume was injected through a septum in stopcock (i.e. below the syringe). In the first method this calibration volume was immediately flushed through the liquid and the apparatus using an appropriate carrier gas. In the second method, the headspace of carrier gas in the syringe was reduced to approximately 1 ml and the upper stopcock was closed. The calibration volume was then injected into the septum of the lower stopcock as explained above and this was then flushed into the apparatus by allowing a few bubbles of carrier gas to enter the apparatus. The calibration volume was then allowed to dissolve in the liquid for ten minutes before being sparged in the usual way. The reason for using both these methods was that the shape of the curve obtained was different in each case and it was important to ascertain that the calculated areas and therefore the volume was the same in each case. The shape of the area curves using the second method more closely resembled those obtained on experimental runs than when using the much quicker first method.

All areas were calculated using a computer integration program. The accuracy of this integration was checked in a number of ways. Firstly, calibration injections were performed in a variety of ways, using different injection rates and different stand times for the same volumes. Also, sample volumes were injected by one author in a blinded manner while another author was responsible for gas analysis and calculation of area and therefore of injected volume. Lastly, the partial pressure-time curves were printed on a dot-matrix printer and the area calculated manually by using Simpson's rule and also by weighing the cut-out paper curves on an accurate balance. The type of calibration injection was shown to have no effect on the volumes measured.

It has been found that supersaturation does not occur providing that atmospheric pressure is maintained inside the apparatus. In addition, it is useful to allow the fluid to sit undisturbed for 10 or 20 minutes after equilibration with test gas to ensure that neither supersaturation nor persistent bubbles affect measurements.

If it is necessary only to measure the content of gas in a fluid, for example, the volume of nitrogen contained in a blood specimen, then equilibration procedures are not required. In this instance, all measurements take 15 minutes or less. This is much faster than existing methods.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A gas investigation apparatus to determine the amount of gas In a liquid, said apparatus comprising:
   (a) a hollow, longitudinally-extending cylindrical barrel for holding a liquid and a sample liquid with gas dissolved therewithin and with an associated gaseous headspace above, said barrel having a lower inlet and an upper outlet, at least a portion thereof being transparent;
   (b) a plunger slidably fitted in a leak-proof manner within said barrel, said barrel containing said sample liquid with said gas dissolved therewithin and with said gaseous headspace above, said plunger being free to slide along the longitudinal length of said barrel, thereby forming a variable volume of air and gas in said headspace above said liquid contained by said plunger in said barrel;
   (c) a gas inlet tube having a lower inlet and an upper outlet within the plunger and extending along the longitudinal axis of said plunger;
   (d) a longitudinally-extending, heat transfer jacket surrounding said hollow, longitudinally-extending cylindrical barrel for the regulations of the temperature of said liquid sample with said gas dissolved therewithin and with said gaseous headspace above, at least a longitudinally-extending portion thereof being transparent;
   (e) an upper valve connected to said upper outlet of said barrel by means of a zero dead-space, butt-end connection;
   (f) selective entry means through said upper valve for admitting a study liquid or tissue suspension into the barrel;
   (g) a lower valve connected to said lower inlet of said gas inlet tube by means of a zero dead-space, butt-end connection;
   (h) inlet conduit means for the selective introduction of test gas, calibration gas, carrier gas, or flushing gas into said gas inlet tube through said lower valve;
   (i) inlet tube means for the selective introduction of a gas sample into said inlet conduit means through said lower valve; and
   (j) exit tube means connected to said upper valve by means of a zero dead-space, butt-end connection, for leading gas exiting from the plunger-position-dependent variable volume of gaseous space at the upper portion of said barrel to a mass spectrometer.

2. The gas investigation apparatus of claim 1 wherein said cylindrical barrel and said heat transfer jacket are entirely transparent.

3. The gas investigation apparatus of claim 2 wherein said cylindrical barrel and said heat transfer jacket are each made out of glass.

4. The gas investigation apparatus of claim 1 wherein said plunger is formed of a rigid synthetic plastic material.

5. The gas investigation apparatus of claim 1 wherein said plunger is formed of an epoxy resin.

6. The gas investigation apparatus of claim 1 wherein said plunger is provided with a central longitudinal bore having an inlet and an outlet, and within said bore of which said gas inlet tube is situated.

7. The gas investigation apparatus of claim 6 wherein said plunger is provided with a ring-shaped tip formed of a synthetic plastic material.

8. The gas investigation apparatus of claim 7 wherein said ring-shaped tip is formed of polytetrafluoroethylene.

9. The gas investigation apparatus of claim 7 wherein said ring-shaped tip is provided with a gas injection tip.

10. The gas investigation apparatus of claim 9 wherein said gas inlet tube is connected at its lower end to said inlet of said bore of said plunger, and is connected at its upper end to said gas injection tip.

11. The gas investigation apparatus of claim 1 wherein said upper valve is a three-way valve or stop cock.

12. The gas investigation apparatus of claim 1 wherein said lower valve is a three-way valve or stop cock.

13. The gas investigation apparatus of claim 1 wherein said exit tube leading between said barrel and said spectrometer includes a further tube for the recycling of gas exiting said barrel back to the barrel.

14. The gas investigation apparatus of claim 1 including a bank of interconnected valves connected to said further tube.

15. The gas investigation apparatus of claim 14 wherein one of said interconnected valves is connected to said lower valve.

16. The gas investigation apparatus of claim 1 wherein said lower valve includes a gas injection port.

17. The gas investigation apparatus of claim 1 wherein said transparent barrel is formed of a transparent synthetic plastic material; wherein said plunger is formed of stainless steel; wherein said heat transfer jacket is formed of transparent synthetic plastic material; and wherein said inlet tube means and said exit tube means are each formed of polytetrafluoroethylene.

18. The gas investigation apparatus of claim 1 wherein said syringe barrel is formed of transparent glass; wherein said syringe plunger is formed of an epoxy resin; wherein said water jacket is formed of a transparent acylate resin; and wherein said inlet tube means and said exit tube means are each formed of polytetrafluoroethylene.

19. The gas investigation apparatus of claim 1, including a temperature probe within said water jacket to measure the temperature of heat transfer liquid.

20. The gas investigation apparatus of claim 1, including a scavenging gas outlet tube connecting the upper valve of said barrel to an atmospheric pressure scavanging system by means of a zero dead-space butt-end connection.

21. The gas investigation apparatus of claim 1, including a liquid trap and filter in said gas sampling exit tube between exit tube means from said barrel to said mass spectrometer.

22. The gas investigation apparatus of claim 1, including an ultrasonic tissue disrupter operatively associated with said cylindrical heat transfer jacket and arranged proximate the upper end of said barrel.

23. In combination
   A) a gas investigation apparatus to determine the amount of gas in a liquid, said apparatus comprising:
      (a) a hollow, longitudinally-extending cylindrical barrel for holding a liquid and a sample liquid with gas dissolved therewithin and with an associated gaseous headspace above, said barrel having a lower inlet and an upper outlet, at least a portion thereof being transparent;
      (b) a plunger slidably fitted in a leak-proof manner within said barrel said barrel containing said sample liquid with said gas dissolved therewithin and with said gaseous headspace above, said plunger being free to slide along the longitudinal length of said barrel, thereby forming a variable volume of air and gas in said headspace above said liquid contained by said plunger in said barrel;
      (c) a gas inlet tube having a lower inlet and an upper outlet within the plunger and extending along the longitudinal axis of said plunger;
      (d) a longitudinally-extending, heat transfer jacket surrounding said hollow, longitudinally-extending cylindrical barrel for the regulation of the temperature of said liquid sample with said gas dissolved therewithin and with said gaseous headspace above, at least a longitudinally-extending portion thereof being transparent;
      (e) an upper valve connected to said upper outlet of said barrel by means of a zero dead-space, butt-end connection;
      (f) selective entry means through said valve for admitting a study liquid or tissue suspension into the barrel;
      (g) a lower valve connected to said lower inlet of said gas inlet tube by means of a zero dead-space, butt-end connection;
      (h) inlet conduit means for the selective introduction of test gas, calibration gas, carrier gas, or flushing gas into said gas inlet tube through said lower valve;
      (i) inlet tube means for the selective introduction of a gas sample into said inlet conduit means through said lower valve; and
      (j) exit tube means connected to said upper valve by means of a zero dead-space, butt-end connection, for leading gas exiting the plunger-position-dependent variable volume of gaseous space from the upper portion of said barrel to a mass spectrometer;
   and
   B) a mass spectrometer operatively connected to said exit tube means.

* * * * *